US008957002B2

(12) United States Patent
Miller et al.

(10) Patent No.: US 8,957,002 B2

(45) Date of Patent: Feb. 17, 2015

(54) DNA MICROARRAY HAVING HAIRPIN PROBES TETHERED TO NANOSTRUCTURED METAL SURFACE

(75) Inventors: Benjamin L. Miller, Penfield, NY (US); Todd D. Krauss, Pittsford, NY (US); Lewis J. Rothberg, Pittsford, NY (US); Hsin-I Peng, Rochester, NY (US)

(73) Assignee: University of Rochester, Rochester, NY (US)

( * ) Notice: Subject to any disclaimer, the term of this patent is extended or adjusted under 35 U.S.C. 154(b) by 969 days.

(21) Appl. No.: 12/265,047

(22) Filed: Nov. 5, 2008

(65) Prior Publication Data

US 2009/0137418 A1 May 28, 2009

Related U.S. Application Data

(60) Provisional application No. 60/985,459, filed on Nov. 5, 2007.

(51) Int. Cl.

*G01N 21/05* (2006.01)

*G01N 21/64* (2006.01)

(Continued)

(52) U.S. Cl.

CPC ............. *C40B 50/18* (2013.01); *B01J 19/0046* (2013.01); *B82Y 30/00* (2013.01); *C12Q 1/6825* (2013.01); *C40B 60/08* (2013.01); *G01N 21/64* (2013.01); *G01N 21/05* (2013.01); *G01N 21/6428* (2013.01); *B01J 2219/00527* (2013.01); *B01J 2219/00576* (2013.01);

(Continued)

(58) Field of Classification Search

USPC ............................................................. 506/9

See application file for complete search history.

(56) References Cited

U.S. PATENT DOCUMENTS 5,215,899 A 6/1993 Dattagupta 5,556,749 A 9/1996 Mitsuhashi et al.

(Continued)

FOREIGN PATENT DOCUMENTS

WO 00/43552 A2 7/2000

WO WO 2004061127 A2 * 7/2004

OTHER PUBLICATIONS

Krusteva et al. "Self-Assembled Gold Nanoparticle/Dendrimer Composite Films for Vapor Sensing Applications" (2002) Nano Letters 2:551-555.*

Haes et al. "A Nanoscale Optical Biosensor: Sensitivity and Selectivity of an Approach Based on the Localized Surface Plasmon Resonance Spectroscopy of Triangular Silver Nanoparticles" (2002) J. Amer. Chem. Soc. 124:10596-10604.*

Stranik et al. "Plasmonic Enhancement of Fluorescence for Sensor Applications" Sensors and Actuators B (2005) 107:148-153.*

(Continued)

*Primary Examiner* — Christopher M Babic

*Assistant Examiner* — Jeremy C Flinders

(74) *Attorney, Agent, or Firm* — LeClairRyan, a Professional Corporation

(57) ABSTRACT

A sensor chip and detection device are disclosed. The sensor chip includes a substrate, at least a portion of which is covered by a metal nanoparticle film; a first nucleic acid molecule that is characterized by being able to (i) self-anneal into a hairpin conformation and (ii) hybridize specifically to a target nucleic acid molecule, the first nucleic acid molecule having first and second ends, which first end is tethered to the metal nanoparticle film; and a first fluorophore bound to the second end of the first nucleic molecule. When the first nucleic acid molecule is in the hairpin conformation, the metal nanoparticle film substantially quenches fluorescent emissions by the first fluorophore, and when the first nucleic acid molecule is in a non-hairpin conformation fluorescent emissions by the first fluorophore are surface plasmon-enhanced.

24 Claims, 14 Drawing Sheets

(51) Int. Cl.

| | |
|---|---|
| ***C40B 50/18*** | (2006.01) |
| ***B01J 19/00*** | (2006.01) |
| ***B82Y 30/00*** | (2011.01) |
| ***C12Q 1/68*** | (2006.01) |
| ***C40B 60/08*** | (2006.01) |
| *C40B 60/12* | (2006.01) |
| *C40B 30/04* | (2006.01) |

(52) U.S. Cl.

CPC .................. *B01J 2219/00596* (2013.01); *B01J 2219/00605* (2013.01); *B01J 2219/00612* (2013.01); *B01J 2219/00626* (2013.01); *B01J 2219/00637* (2013.01); *B01J 2219/00648* (2013.01); *B01J 2219/00659* (2013.01); *B01J 2219/00702* (2013.01); *B01J 2219/00722* (2013.01)

USPC ............ 506/9; 436/172; 536/22.1; 435/287.2

(56) References Cited

U.S. PATENT DOCUMENTS

| | | | | |
|---|---|---|---|---|
| 5,925,517 | A | 7/1999 | Tyagi et al. | |
| 6,114,121 | A | 9/2000 | Fujiwara et al. | |
| 6,194,155 | B1 | 2/2001 | Cohen | |
| 6,251,588 | B1 | 6/2001 | Shannon et al. | |
| 6,277,607 | B1 | 8/2001 | Tyagi et al. | |
| 6,312,906 | B1 * | 11/2001 | Cass et al. | 435/6 |
| 6,355,437 | B1 | 3/2002 | Neri et al. | |
| 6,365,729 | B1 | 4/2002 | Tyagi et al. | |
| 6,380,377 | B1 | 4/2002 | Dattagupta | |
| 7,070,933 | B2 | 7/2006 | Browne | |
| 7,442,510 | B2 | 10/2008 | Miller et al. | |
| 2003/0013109 | A1 | 1/2003 | Ballinger et al. | |
| 2003/0054346 | A1 | 3/2003 | Shannon et al. | |
| 2003/0143535 | A1 | 7/2003 | Lyamichev et al. | |
| 2003/0148401 | A1 | 8/2003 | Agrawal et al. | |
| 2004/0180379 | A1 * | 9/2004 | Van Duyne et al. | 435/7.1 |
| 2005/0079506 | A1 | 4/2005 | Leon et al. | |
| 2005/0164320 | A1 | 7/2005 | McDevitt et al. | |
| 2005/0196876 | A1 | 9/2005 | Chan et al. | |
| 2007/0059693 | A1 | 3/2007 | Miller et al. | |
| 2007/0181900 | A1 | 8/2007 | Sato et al. | |
| 2008/0014581 | A1 * | 1/2008 | Nakahara et al. | 435/6 |

OTHER PUBLICATIONS

Pompa et al., Nature Nanotechnology, 2006, 1: 126-130.*

Zhang et al., J. Phys. Chem. B, 2006, 110:2387-2392.*

Park et al., J. Phys. Chem B, 2002, 106:8667-8670.*

Lakowicz et al., Biotechiques, 2003, 34(1):62-68.*

Stimpson et al., Proc. Natl. Acad. Sci., 1995, 92:6379-6383.*

Leff et al., Langmuir, 1996, 12:4723-4730.*

Freeman et al., Science, 1995, 267:1629-1633.*

Grabar et al. (Langmuir, 1996, 12:2353-2361).*

Du et al. (J. Am. Chem. Soc., 2005, 127:7932-7940).*

International Search Report for International Patent Application No. PCT/US08/82431 (May 4, 2009).

Written Opinion of the International Searching Authority for International Patent Application No. PCT/US08/82431 (Apr. 24, 2009).

Bonnet et al., "Thermodynamic Basis of the Enhanced Specificity of Structured DNA Probes," Proc. Natl. Acad. Sci. USA 96:6171-6176 (1999).

Dubertret et al., "Single-Mismatch Detection Using Gold-Quenched Fluorescent Oligonucleotides," Nat. Biotech. 19:365-370 (2001).

Broude, "Stem-loop Oligonucleotides: A Robust Tool for Molecular Biology and Biotechnology," Trends in Biotechnology 20(6):249-56 (2002).

Elsayed et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. 127:845-9 (2003).

Kushon et al., "Effect of Secondary Structure on the Thermodynamics and Kinetics of PNA Hybridization to DNA Hairpins," J. Am. Chem. Soc. 123(44):10805-13 (2001).

Park et al., "Rapid Identification of *Candida dubliniensis* Using a Species-Specific Molecular Beacon," Journal of Clinical Microbiology 38(8):2829-36 (2000).

Riccelli et al., "Hybridization of Single-stranded DNA Targets to Immobilized Complementary DNA Probes: Comparison of Hairpin Versus Linear Capture Probes," Nucleic Acids Research 29(4):996-1004 (2001).

Du et al., "Hybridization-Based Unquenching of DNA Hairpins on Au Surfaces: Prototypical "Molecular Beacon" Biosensors," J. Chem. Soc. 125:4013-4013 (2003).

* cited by examiner

SEQUENCE LISTING

<160> NUMBER OF SEQ ID NOS: 12

<210> SEQ ID NO 1
<211> LENGTH: 34
<212> TYPE: DNA
<213> ORGANISM: Artificial
<220> FEATURE:
<223> OTHER INFORMATION: B. anthracis pag gene hairpin

<400> SEQUENCE: 1
tcgttagtgt taggaaaaaa tcaaacactc gcga 34

<210> SEQ ID NO 2
<211> LENGTH: 34
<212> TYPE: DNA
<213> ORGANISM: Artificial
<220> FEATURE:
<223> OTHER INFORMATION: Hairpin target of SEQ ID NO: 1

<400> SEQUENCE: 2
tcgcgagtgt ttgatttttt cctaacacta acga 34

<210> SEQ ID NO 3
<211> LENGTH: 18
<212> TYPE: DNA
<213> ORGANISM: Artificial
<220> FEATURE:
<223> OTHER INFORMATION: E. coli K12 gene hairpin

<400> SEQUENCE: 3
gttccgtctt gtcggaac 18

<210> SEQ ID NO 4
<211> LENGTH: 25
<212> TYPE: DNA
<213> ORGANISM: Artificial
<220> FEATURE:
<223> OTHER INFORMATION: E. coli K12 gene hairpin

<400> SEQUENCE: 4
cggatctcga tgagctgcag atccg 25

<210> SEQ ID NO 5
<211> LENGTH: 30

-continued

<212> TYPE: DNA
<213> ORGANISM: Artificial
<220> FEATURE:
<223> OTHER INFORMATION: E. coli TIR gene hairpin

<400> SEQUENCE: 5
agcataggga ccgtgcagaa tccgtatgct 30

<210> SEQ ID NO 6
<211> LENGTH: 38
<212> TYPE: DNA
<213> ORGANISM: Artificial
<220> FEATURE:
<223> OTHER INFORMATION: K. pneumoniae blaSHV gene hairpin with synthetic stem

<400> SEQUENCE: 6
aaatttcttt cccatgatga gcacctttaa agaaattt 38

<210> SEQ ID NO 7
<211> LENGTH: 47
<212> TYPE: DNA
<213> ORGANISM: Artificial
<220> FEATURE:
<223> OTHER INFORMATION: E. coli plasmid pARS3 gene hairpin

<400> SEQUENCE: 7
cgctctggaa atgttcaatg aggactatgt gacattcccc agggacg 47

<210> SEQ ID NO 8
<211> LENGTH: 18
<212> TYPE: DNA
<213> ORGANISM: Artificial
<220> FEATURE:
<223> OTHER INFORMATION: Hairpin target of SEQ ID NO: 3

<400> SEQUENCE: 8
gttccgacaa gacggaac 18

<210> SEQ ID NO 9
<211> LENGTH: 25
<212> TYPE: DNA
<213> ORGANISM: Artificial
<220> FEATURE:
<223> OTHER INFORMATION: Hairpin target of SEQ ID NO: 4

<400> SEQUENCE: 9
cggatctgca gctcatcgag atccg 25

<210> SEQ ID NO 10
<211> LENGTH: 30
<212> TYPE: DNA
<213> ORGANISM: Artificial
<220> FEATURE:
<223> OTHER INFORMATION: Hairpin target of SEQ ID NO: 5

<400> SEQUENCE: 10
agcatacgga ttctgcacgg tccctatgct 30

<210> SEQ ID NO 11
<211> LENGTH: 38
<212> TYPE: DNA
<213> ORGANISM: Artificial
<220> FEATURE:
<223> OTHER INFORMATION: Hairpin target of SEQ ID NO: 6

<400> SEQUENCE: 11

-continued

```
aaatttcttt aaaggtgctc atcatgggaa agaaattt                         38


<210> SEQ ID NO 12
<211> LENGTH: 47
<212> TYPE: DNA
<213> ORGANISM: Artificial
<220> FEATURE:
<223> OTHER INFORMATION: Hairpin target of SEQ ID NO: 7

<400> SEQUENCE: 12

cgtccctggg gaatgtcaca tagtcctcat tgaacatttc cagagcg               47
```

DNA MICROARRAY HAVING HAIRPIN PROBES TETHERED TO NANOSTRUCTURED METAL SURFACE

The present application claims the priority benefit of U.S. Provisional Patent Application Ser. No. 60/985,459, filed Nov. 5, 2007, which is hereby incorporated by reference in its entirety.

FIELD OF THE INVENTION

The present invention relates to hybridization-based biosensors containing hairpin probes and their use in identifying target nucleic acids in samples.

BACKGROUND OF THE INVENTION

Recent intense interest in the use of rapid genetic analysis as a tool for understanding biological processes (Wodicka et al., *J. Nat. Biotechnol.* 15:1359-1367 (1997); Iyer et al., *Science* 283:83-87 (1999)), in unlocking the underlying molecular causes of disease, and in the development of biosensors, has led to a need for new sensitive and arrayable chip-based analytical tools. Of high importance is the need for techniques that do not require labeling of the target sample (Sando et al., *J. Am. Chem. Soc.* 124:2096-2097 (2002), since that increases the time, cost, and potential for error inherent in the analysis. In the context of solution-phase assays, the molecular beacon concept has proven itself to be both sensitive and reliable (Broude, *Trends Biotech.* 20:249-256 (2002); Dubertret et al., *Nature Biotech.* 19:365-370 (2001)). Molecular beacons consist of a DNA hairpin functionalized at one end with a fluorophore, and at the other with a quenching agent (Tyagi et al., *Nat. Biotechnol.* 14:303-308 (1996); Joshi et al., *Chem. Commun.* 1(6):549-550 (2001)). In the absence of the target DNA sequence, the quencher is brought in close proximity to the fluorophore, and no signal is generated. Addition of the target sequence leads to hairpin unfolding, concomitant duplex formation, and signal generation.

Although a few reports of surface-immobilized molecular beacons have appeared in the literature (Fang et al., *J. Am. Chem. Soc.* 121:2921-2922 (1999); Wang et al., *Nucl. Acids. Res.* 30:e61 (2002)), it is believed that these approaches employ an attached single molecule as quencher, while the material on (or in) which the hairpin is immobilized serves only a passive role. As part of a general program aimed at developing "label-free" optical biosensors (Chan et al., *J. Am. Chem. Soc.* 123:11797-11798 (2001)), it was of interest, therefore, to investigate whether the substrate material itself could be used as a quenching agent. Using the substrate itself as the quenching agent significantly decreases the complexity of the synthetic DNA probe hairpin, because attachment of a separate quencher is unnecessary. This approach has been successfully demonstrated using planar gold surfaces that effectively serve as both anchoring points and quenchers for DNA hairpin probes bearing an attached fluorophore (see U.S. Patent Publ. No. 20070059693 and co-pending U.S. patent application Ser. No. 11/838,616).

One straightforward approach for improving the sensitivity of the DNA hairpin array is to increase the intensity of the fluorescence for a given excitation intensity. Simply increasing the intensity of the excitation source is not a viable route to increased signals, because many fluorescent labels will photobleach completely within a fraction of a second for high excitation powers. For example, because rhodamine—comparatively a very photostable dye—photobleached at I~1

$kW/cm^2$, it is highly unlikely that changing dyes will improve the signal. Clearly, new approaches are needed to increase the signal from these devices.

An additional limitation arises when using metal films as quenching surfaces for fluorophore-functionalized DNA hairpin probes. Typically, these films are sufficiently thick that light does not pass through them (i.e., they are opaque or near-opaque). This constrains visualization of the chip to only one side. It would be desirable, therefore, to prepare a sensor chip that is not so constrained.

The present invention is directed to overcoming these and other deficiencies in the art.

SUMMARY OF THE INVENTION

A first aspect of the present invention relates to a sensor chip that includes: a substrate, at least a portion of which is covered by a metal nanoparticle film; a first nucleic acid molecule that is characterized by being able to (i) self-anneal into a hairpin conformation and (ii) hybridize specifically to a target nucleic acid molecule, the first nucleic acid molecule having first and second ends, which first end is tethered to the metal nanoparticle film; and a first fluorophore bound to the second end of the first nucleic molecule. When the first nucleic acid molecule is in the hairpin conformation, the metal nanoparticle film substantially quenches fluorescent emissions by the first fluorophore, and when the first nucleic acid molecule is in a non-hairpin conformation fluorescent emissions by the first fluorophore are surface plasmon-enhanced.

A second aspect of the present invention relates to a biological sensor device that includes a sensor chip according to the first aspect of the present invention; a light source that illuminates the sensor chip at a wavelength suitable to induce fluorescent emissions by the fluorophore(s); and a detector positioned to detect fluorescent emissions by the fluorophore(s).

A third aspect of the present invention relates to a method of detecting the presence of a target nucleic acid molecule in a sample. This method is carried out by exposing the sensor chip according to the first aspect of the present invention to a sample under conditions effective to allow any target nucleic acid molecule in the sample to hybridize to the nucleic acid molecules, causing the nucleic acid molecules to adopt the non-hairpin conformation; illuminating the sensor chip with light sufficient to cause emission of fluorescence by the fluorophore(s); and determining whether or not the sensor chip emits fluorescent emissions of one or more of the fluorophores upon said illuminating, wherein fluorescent emission by the sensor chip indicates that a nucleic acid molecule is in the non-hairpin conformation and therefore that its target nucleic acid molecule is present in the sample.

A fourth aspect of the present invention relates to a method of making a sensor chip according to the first aspect of the present invention. This method includes at least partially coating a substrate with metal nanoparticles to form metal nanoparticle film; and covalently attaching one or more nucleic acid molecules to the metal nanoparticle film. The one or more nucleic acid molecules are different from one another and characterized by being able to (i) self-anneal into a hairpin conformation and (ii) hybridize specifically to a target nucleic acid molecule. Each of the plurality of nucleic acid molecules has first and second ends, which first end is attached to the metal nanoparticle film and which second end is bound to a fluorophore.

The present invention affords self-labeled nucleic acid detection systems that are capable of achieving a dramatic (~10-fold) fluorescence enhancement over detection systems that utilize a planar Au quenching surface. The examples presented herein demonstrate that the surface topography of the quenching nanoparticle substrate and the amount of Ag that was deposited onto the surface can be varied by controlling the Ag exposure time in a constant concentration of $AgNO_3$ solution. Furthermore, detection performance and signals were dependent on both the surface topography/NP coverage and the distance between the fluorophore and the Ag substrate surface. These findings collectively indicated the importance of local probe density adjustment and probe length selection for detection performance. The ability to pattern the probe immobilization on the surface by controlling the spacing between nanoparticles can avoid or minimize the need for spacer molecules that are required for optimal performance on solid Au surfaces. Of further interest is the fact that the low-exposure nanoparticle substrates are transparent, which should allow for their inclusion in a flow-through device in which either imaging or illumination occurs from the opposite face rather than the functionalized face that is exposed to the sample.

DETAILED DESCRIPTION OF THE INVENTION

Figure 1:
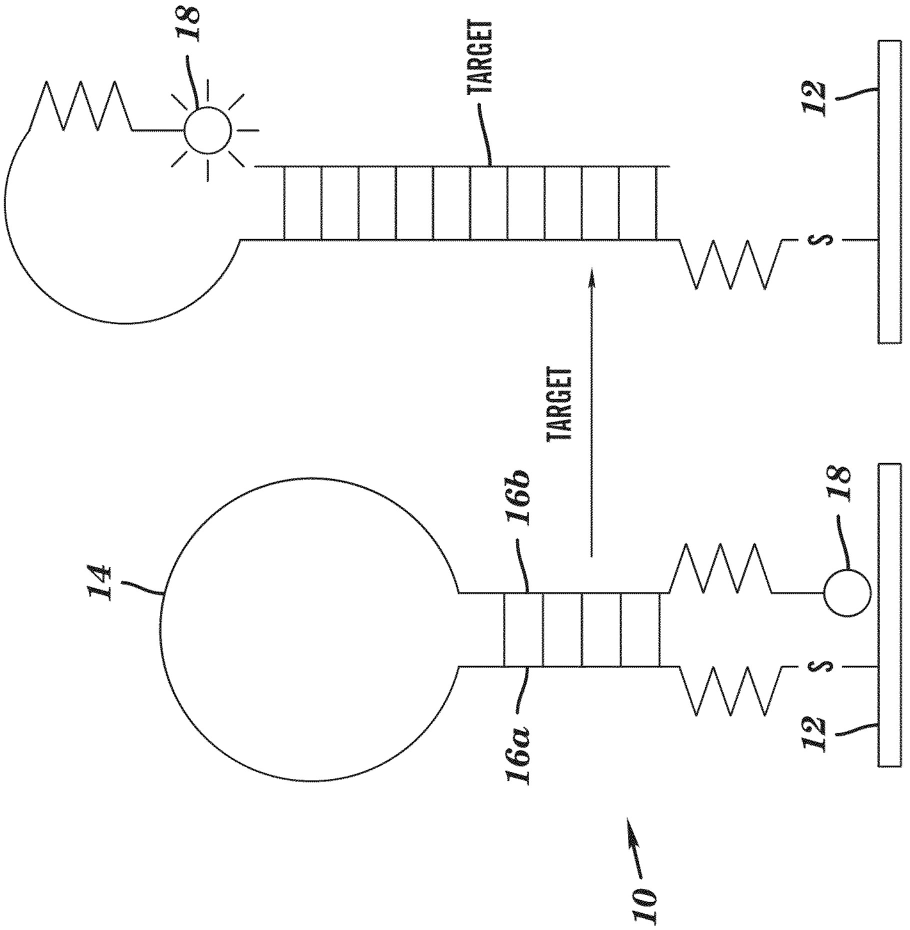
FIG. 1 illustrates a sensor chip of the present invention. A hairpin nucleic acid molecule is immobilized at one end thereof to a metal nanoparticle film on a substrate, and the other end thereof has a fluorophore attached thereto. In the hairpin conformation, the fluorophore is in sufficiently close proximity to the metal nanoparticle film such that fluorescent emissions of the fluorophore are quenched. In the presence of a target nucleic acid molecule, the hairpin conformation is lost, resulting in fluorescent emissions that are no longer quenched by the metal nanoparticle film but instead are surface-plasmon enhanced.

One aspect of the present invention relates to a sensor chip that can be used to detect the presence of target nucleic acid molecules in a sample. As shown in FIG. 1, the sensor chip 10 includes: a substrate 12, at least a portion of which is covered by a metal nanoparticle film; one or more nucleic acid molecules 14 (i.e., as probes) each having first and second ends with the first end bound to the metal nanoparticle film, a first region 16*a*, and a second region 16*b* complementary to the first region; and a first fluorophore 18 bound to the second end of the nucleic acid molecule 14.

Suitable nucleic acid probes can be DNA, RNA, or PNA. The nucleic acid probes of the present invention can also possess one or more modified bases, one or more modified sugars, one or more modified backbones, or combinations thereof. The modified bases, sugars, or backbones can be used either to enhance the affinity of the probe to a target nucleic acid molecule or to allow for binding to the metal nanoparticle film as described hereinafter. Exemplary forms of modified bases are known in the art and include, without limitation, alkylated bases, alkynylated bases, thiouridine, and G-clamp (Flanagan et al., *Proc. Natl. Acad. Sci. USA* 30:3513-3518 (1999), which is hereby incorporated by reference in its entirety). Exemplary forms of modified sugars are known in the art and include, without limitation, LNA, 2'-O-methyl, 2'-O-methoxyethyl, and 2'-fluoro (see, e.g., Freier and Attmann, *Nucl. Acids Res.* 25:4429-4443 (1997), which is hereby incorporated by reference in its entirety). Exemplary forms of modified backbones are known in the art and include, without limitation, phosphoramidates, thiophosphoramidates, and alkylphosphonates. Other modified bases, sugars, and/or backbones can, of course, be utilized.

With the first and second regions 16*a*,16*b* of the nucleic acid probes 14 being complementary to one another, the nucleic acid probes have, under appropriate conditions, either (i) a hairpin conformation with the first and second regions hybridized together (shown on the left side of FIG. 1) or (ii) a non-hairpin conformation (shown on the right side of FIG. 1). The conditions under which the hairpin conformation exists is when the nucleic acid probe is maintained below its melting temperature (i.e., considering the length of the first and second regions, the GC content of those regions, and salt concentration), and typically when the target nucleic acid is not present. The conditions under which the non-hairpin conformation exists are either when the first nucleic acid is maintained above its melting temperature and/or when the probe is hybridized to its target nucleic acid (as shown in FIG. 1).

The overall length of the nucleic acid probe is preferably between about 12 and about 60 nucleotides. The probe length is more preferably between about 20 and about 50 nucleotides or between about 25 and about 45 nucleotides, most preferably between about 30 and about 40 nucleotides. It should be appreciated, however, that longer or shorter nucleic acids can certainly be used. The first and second regions of the nucleic acid probes are preferably at least about 4 nucleotides in length, more preferably at least about 5 nucleotides in length or at least about 6 nucleotides in length. In the preferred embodiments described above, the first and second regions can be up to about 28 nucleotides in length, depending on the overall length of the nucleic acid probe and the size of a loop region present between the first and second regions. It is believed that a loop region is needed to allow the hairpin to form, and the loop region preferably contains at least about 4 or 5 nucleotides. The first and second regions can be perfectly matched (i.e., having 100 percent complementary sequences that form a perfect stem structure of the hairpin conformation) or less than perfectly matched (i.e., having non-complementary portions that form bulges within a non-perfect stem structure of the hairpin conformation). When the first and second regions are not perfectly matched the first and second regions can be the same length or they can be different in length, although they should still have at least 4 complementary nucleotides.

Nucleic acid probes of the present invention can have their entire length or any portion thereof targeted to hybridize to the target nucleic acid molecule, which can be RNA or DNA. Thus, the entire probe can hybridize to a target sequence of the target nucleic acid molecule or, alternatively, a portion thereof can hybridize to a target sequence of the target nucleic acid molecule. When less than the entire nucleic acid probe is intended to hybridize to the target nucleic acid molecule, the portion thereof that does hybridize (to the target nucleic acid molecule) should be at least about 50 percent, preferably at least about 60 or 70 percent, more preferably at least about 80 or 90 percent, and most preferably at least about 95 percent of the nucleic acid probe length. When only a portion of the nucleic acid probe is intended to hybridize to the target nucleic acid molecule, that portion can be part of the first region, part of the second region, or spanning both the first and second regions. As used herein to describe the portion of the probe that hybridizes to a target nucleic acid, the phrase "substantially the entire length thereof" is intended to mean not more than two probe nucleotides, preferably not more than one probe nucleotide, that do not hybridize to the target over the length of the probe.

A number of preferred hairpin probes are identified in co-pending U.S. Patent Application Publ. No. 20070059693 and U.S. patent application Ser. No. 11/838,616 to Miller et al., each of which is hereby incorporated by reference in its entirety.

Selection of suitable nucleic acid molecules for use as probes can be achieved by (i) identifying an oligonucleotide that can hybridize to the target nucleic acid and then designing a nucleic acid probe that includes the oligonucleotide as a component part of the first and/or second region, and optionally as a component part of any loop region between the first and second regions; (ii) by identifying naturally occurring hairpin structures within the predicted folding structure of a target nucleic acid molecule, as described in co-pending PCT Publ. No. WO 2005/104813 and U.S. Pat. No. 7,442,510, both to Miller et al., each of which is hereby incorporated by reference in its entirety; or (iii) using a combination of the above procedures, modifying a portion of a naturally occurring hairpin structure, e.g., modifying one or more bases in the first or second region to increase the stability of the resulting probe or the stability of the probe-target interaction.

Referring again to FIG. 1, while the probe remains in the hairpin conformation the fluorophore 18 bound to the second end of the nucleic acid probe is brought into sufficiently close proximity to the metal nanoparticle film such that the metal nanoparticle film substantially quenches fluorescent emissions by the fluorophore. As discussed hereinafter, the rate of energy transfer is dependent upon the distance separating the fluorophore and the metal nanoparticle film. In contrast, while the probe remains in the non-hairpin conformation, the fluorophore 18 bound to the second end of the nucleic acid probe is no longer constrained in proximity to the metal nanoparticle film. As a result of its physical displacement away from the metal nanoparticle film, fluorescent emissions by the fluorophore 18 are substantially free of any quenching and, instead, the fluorescent emissions of the fluorophore are surface plasmon enhanced. This results in an order of magnitude gain in fluorescent intensity, allowing for reliable detection of small quantities of target nucleic acid.

Local surface plasmon resonance (LSPR) is a phenomenon caused by resonant light excitation of a collective electron oscillation in a metal particle, called a surface plasmon. For noble metals, the damping of this oscillation (proportional to the imaginary component of the metal dielectric constant) is very weak leading to giant electric field strengths near the particle surface (Moskovits, *Rev. Mod. Phys.*, 57:783-826 (1985); Yang et al., *J. Chem. Phys.*, 103:869-875 (1995), each of which is hereby incorporated by reference in its entirety). These scattered electric fields can couple strongly to radiative modes of local transition dipoles, thereby creating a significant enhancement of over 15 orders of magnitude in certain optical properties such as Raman scattering of adsorbed molecules (Nie et al., *Science* 275:1102-1106 (1997); Michaels et al., *J. Am. Chem. Soc.* 121:9932-9939 (1999); Pan et al., *J. Phys. Chem. B* 110:17383-17387 (2006); Wang et al., *Proc. Natl. Acad. Sci. USA* 100:8638-8643 (2003), each of which is hereby incorporated by reference in its entirety).

Nonradiative energy transfer from a photoexcited dye molecule to the metal causes fluorescence quenching of the dye, and this effect is precisely why the metal-immobilized fluorophore-functionalized DNA hairpin device does not fluoresce when the dye molecule is maintained in close proximity to the metal nanoparticle film (i.e., in absence of complementary DNA). Fluorescence quenching on gold surfaces was also recently observed for CdSe NCs (Shimizu et al., *Phys. Rev. Lett.* 89:117401-117404 (2002), which is hereby incorporated by reference in its entirety). For a noble metal nanoparticle (as opposed to a planar surface), energy transfer is still fast enough to suppress fluorescence from single surface bound dye molecules (Nie et al., *Science* 275:1102-1106 (1997); Michaels et al., *J. Am. Chem. Soc.* 121:9932-9939 (1999); Pan et al., *J. Phys. Chem. B* 110:17383-17387 (2006); Wang et al., *Proc. Natl. Acad. Sci. USA* 100:8638-8643 (2003), each of which is hereby incorporated by reference in its entirety). However, upon displacement of only a nanometer or two from the surface, coupling between molecular and metallic electronic levels is inefficient and quenching of fluorescence no longer occurs. With respect to immobilized hairpin DNA probes, upon target recognition the fluorophore is displaced by on the order of 5-10 nm depending on the length of the oligonucleotide probe (3.4 nm per 10 base pairs). This short distance places the dye directly in the giant electric field region arising from the local surface plasmon of the nanoparticle, which should greatly enhance absorption and fluorescence of the dye molecule. Further enhancements are possible through abrupt shape features that produce enhanced electric fields through a lightening rod effect (Gersten et al., *J. Chem. Phys.* 73:3023-3037 (1980), which is hereby incorporated by reference in its entirety). Thus, using surfaces tailored to exhibit a large LSPR effect, it is expected that increases of several orders of magnitude are possible for the signal from the molecular beacon array.

The metal nanoparticle film on substrate 12 is capable of quenching or absorbing the fluorescent emissions of the fluorophore within the desired bandwidth. The metal nanoparticle film can exist as either a continuous film or a discontinuous film applied to discrete locations on the substrate. The substrate is preferably light transmissive, and it can be formed of a non-quenching material (such as an oxide glass of polymer, e.g., PDMS) or a quenching material (such as a different metal than that used to form the metal nanoparticle film). As described below, a number of approaches exist for applying the metal nanoparticle film onto substrate 12.

One approach involves precipitation of Ag using the Tollens silver mirror reaction. To facilitate binding between the silver mirror and the substrate, the substrate is preferably cleaned and washed, and then coated with a thin chromium layer via vapor deposition (see Du et al., *J. Am. Chem. Soc.* 127:7932-40 (2005), which is hereby incorporated by reference in its entirety). Thereafter, KOH can be used to precipitate $AgNO_3$ and then dropwise introduction of 15 M concentrated ammonium hydroxide redissolves the precipitate via formation of $[Ag(NH_3)_2]^+$. Glass substrate left in this solution for several minutes up to about an hour will then be treated with dextrose (added to a concentration of 0.25 M). Device performance is strongly dependent on the amount of Ag present on the surface. Attachment of thiolated hairpins to the silver surface can be carried out according to known procedures (e.g., U.S. Patent Publ. No. 20070059693 to Miller et al. and U.S. patent application Ser. No. 11/838,616 to Miller et al., each of which is hereby incorporated by reference in its entirety).

According to a second approach, glass substrate can be silanized according to known procedures (e.g., 1% 3-mercaptopropryltrimethoxy silane (MPTS) in 95% methanol acidified with 1 mM acetic acid for 30 minutes). Following silanization and cleaning, slides can be coated with silver nanoparticles using a protocol based on that described by Sabanayagam et al., *Nucleic Acids Res.* 35(2):e13 (2007), which is hereby incorporated by reference in its entirety). The silanized glass slides can be incubated overnight (up to ~18 hrs) in a solution of $AgNO_3$ dissolved to a concentration of 10 mM in anhydrous or hydrous N,N-dimethylformamide (DMF). Using 10 mM $AgNO_3$ solution, optimal Ag nanoparticles film deposition was achieved in about 20 to about 60 minutes.

According to a third approach, nanosphere lithography (NSL) can be employed (Hulteen et al., *J. Phys. Chem. B* 103:3854-3863 (1999); Haynes et al., *J. Phys. Chem. B* 105:5599-5611 (2001), each of which is hereby incorporated by reference in its entirety). Briefly, 5 µl of carboxyl terminated polystyrene nanospheres (Interfacial Dynamics Corporation) with a desired diameter (up to several hundred nm in diameter) can be drop cast onto a glass substrate and then slow evaporation of the water will cause the nanospheres to self assemble into a hexagonally close packed monolayer. The nanosphere monolayer acts as a mask for deposition of evaporated silver or gold. Subsequent sonication in ethanol removes the spheres and leaves behind an array of uniformly spaced, triangularly shaped metal nanoparticles (Haynes et al., *J. Phys. Chem. B*, 105, 5599-5611 (2001), which is hereby incorporated by reference in its entirety). Smaller nanospheres can reduce the dimension of the nanoparticle deposits and also reduce the spacing between them, whereas larger nanospheres can increase the dimension of the nanoparticle deposits and also increase the spacing between them.

Preferred materials for formation of the metal nanoparticle film include conductive metals or metal alloys, which offer the ability to completely or nearly completely quench the fluorescence emissions of the fluorophore. Suitable conductive metals or metal alloys include, without limitation, gold, silver, platinum, titanium, copper, gallium, aluminum, p-doped silicon (e.g., $(CH_3)_2Zn$, $(C_2H_5)_2Zn$, $(C_2H_5)_2Be$, $(CH_3)_2Cd$, $(C_2H_5)_2Mg$, B, Al, Ga, or In dopants), n-doped silicon (e.g., $H_2Se$, $H_2S$, $CH_3Sn$, $(C_2H_5)_3S$, $SiH_4$, $Si_2H_6$, P, As, or Sb dopants), and doped germanium. Of these, gold, silver, and platinum are typically preferred.

According to one preferred embodiment, the substrate is an oxide glass and the metal nanoparticle film is formed of silver nanoparticles.

According to another preferred embodiment, the substrate includes a substantially planar gold surface coated onto another material (e.g., chromium-coated oxide glass or polymer) and the metal nanoparticle film is applied to the gold surface.

Regardless of the approach for forming the metal nanoparticle film, the resulting film should be characterized by fractal roughness that is sufficient to allow both quenching and surface plasmon enhancement of fluorescent emission depending on the configuration of the nucleic acid probe and the proximity of the fluorophore to the metal nanoparticle film. The metal nanoparticle film is preferably translucent (e.g., having a thickness than it less than about 100 nm, more preferably less than about 80 nm, 70 nm, 60 nm, or 50 nm, and most preferably less than about 40 nm or 30 nm). In certain embodiments, the metal nanoparticle film is preferably characterized by surface roughness of between about 0.7 nm and about 3 nm, more preferably between about 1 nm and about 2.4 nm, most preferably between about 1 nm and about 2 nm.

The nucleic acid probe can be bound to the metal nanoparticle film using known nucleic acid-binding chemistry or by physical means, such as through ionic, covalent or other forces well known in the art (see, e.g., Dattagupta et al., *Analytical Biochemistry* 177:85-89 (1989); Saiki et al., *Proc. Natl. Acad. Sci. USA* 86:6230-6234 (1989); Gravitt et al., *J. Clin. Micro.* 36:3020-3027 (1998), each of which is hereby incorporated by reference in its entirety). Of these approaches, covalent binding is preferred because the sensor chip will be more durable for repeated use. Either a terminal base or another base near the terminal base can be bound to the metal nanoparticle film. For example, a terminal nucleotide base of the nucleic acid probe can be modified to contain a reactive group, such as (without limitation) carboxyl, amino, hydroxyl, thiol, or the like, thereby allowing for coupling of the nucleic acid probe to the metal nanoparticle film.

The fluorophore can be any fluorophore capable of being bound to a nucleic acid molecule. Suitable fluorophores include, without limitation, fluorescent dyes, proteins, and semiconductor nanocrystal particles. Of these, dyes are preferred due to their size constraints and the commercial availability of dye-labeled nucleic acid molecules. The fluorophore used in the present invention is characterized by a fluorescent emission maximum that is detectable either visually or using optical detectors of the type known in the art. Fluorophores having fluorescent emission maxima in the visible spectrum are preferred.

Exemplary dyes include, without limitation, CY2™, YO-PRO™-1, YOYO™-1, Calcein, FITC, FLUORX™, ALEXA™, Rhodamine 110, 5-FAM, OREGON GREEN™ 500, OREGON GREEN™ 488, RIBOGREEN™, RHODAMINE GREEN™, Rhodamine 123, MAGNESIUM GREEN™, CALCIUM GREEN™, TO-PRO™-1, TOTO®-1, JOE, BODIPY® 530/550, Dil, BODIPY® TMR, BODIPY® 558/568, BODIPY® 564/570, CY3™, ALEXA™ 546, TRITC, MAGNESIUM ORANGE™, Phycoerythrin R&B, Rhodamine Phalloidin, CALCIUM ORANGE™, Pyronin Y, Rhodamine B, TAMRA, RHODAMINE RED™, CY3.5™, ROX, CALCIUM CRIMSON™, ALEXA™ 594, TEXAS RED®, Nile Red, YO-PRO™-3, YOYO™-3, R-phycocyanin, C-Phycocyanin, TO-PRO™-3, TOTO®-3, DiD DilC(5), CY5™ Thiadicarbocyanine, and CY5.5™. Other dyes now known or hereafter developed can similarly be used as long as their excitation and emission characteristics are compatible with the light source and non-interfering with other fluorophores that may be present (i.e., not capable of participating in significant fluorescence resonant energy transfer or FRET).

Attachment of dyes to the opposite end of the nucleic acid probe can be carried using any of a variety of known techniques allowing, for example, either a terminal base or another base near the terminal base to be bound to the dye. For example, 3'-tetramethylrhodamine (TAMRA) may be attached using commercially available reagents, such as 3'-TAMRA-CPG, according to manufacturer's instructions (Glen Research, Sterling, Va.). Other exemplary procedures are described in, e.g., Dubertret et al., *Nature Biotech.* 19:365-370 (2001); Wang et al., *J. Am. Chem. Soc.,* 125:3214-3215 (2003); *Bioconjugate Techniques*, Hermanson, ed. (Academic Press) (1996), each of which is hereby incorporated by reference in its entirety.

Exemplary proteins include, without limitation, both naturally occurring and modified green fluorescent proteins (Prasher et al., *Gene* 111:229-233 (1992); PCT Application WO 95/07463, each of which is hereby incorporated by reference in its entirety) from various sources such as *Aequorea* and *Renilla*; both naturally occurring and modified blue fluorescent proteins (Karatani et al., *Photochem. Photobiol.* 55(2):293-299 (1992); Lee et al., *Methods Enzymol.* (*Biolumin. Chemilumin.*) 57:226-234 (1978); Gast et al., *Biochem. Biophys. Res. Commun.* 80(1):14-21 (1978), each of which is hereby incorporated by reference in its entirety) from various sources such as *Vibrio* and *Photobacterium*; and phycobiliproteins of the type derived from cyanobacteria and eukaryotic algae (Apt et al., *J. Mol. Biol.* 238:79-96 (1995); Glazer, *Ann. Rev. Microbiol.* 36:173-198 (1982); Fairchild et al., *J. Biol. Chem.* 269:8686-8694 (1994); Pilot et al., *Proc. Natl. Acad. Sci. USA* 81:6983-6987 (1984); Lui et al., *Plant Physiol.* 103:293-294 (1993); Houmard et al., *J. Bacteriol.* 170:5512-5521 (1988), each of which is hereby incorporated by reference in its entirety), several of which are commercially available from ProZyme, Inc. (San Leandro, Calif.). Other fluorescent proteins now known or hereafter developed can similarly be used as long as their excitation and emission characteristics are compatible with the light source and non-interfering with other fluorophores that may be present.

Attachment of fluorescent proteins to the opposite end of the nucleic acid probe can be carried using any of a variety of known techniques, for example, either a terminal base or another base near the terminal base can be bound to the fluorescent protein. Procedures used for tether dyes to the nucleic acid can likewise be used to tether the fluorescent protein thereto. These procedures are generally described in, e.g., *Bioconjugate Techniques*, Hermanson, ed. (Academic Press) (1996), which is hereby incorporated by reference in its entirety.

Nanocrystal particles or semiconductor nanocrystals (also known as QUANTUM DOT™-particles), whose radii are smaller than the bulk exciton Bohr radius, constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) as the size of the nanocrystals gets smaller.

The core of the nanocrystal particles is substantially monodisperse. By monodisperse, it is meant a colloidal system in which the suspended particles have substantially identical size and shape, i.e., deviating less than about 10% in rms diameter in the core, and preferably less than about 5% in the core.

Particle size can be between about 1 nm and about 1000 nm in diameter, preferably between about 2 nm and about 50 nm, more preferably about 5 nm to about 20 nm (such as about 5, 6, 7, 8, 9, 10, 11, 12, 13, 14, 15, 16, 17, 18, 19, or 20 nm).

When capped nanocrystal particles are illuminated with a primary light source, a secondary emission of light occurs of a frequency that corresponds to the band gap of the semiconductor material used in the nanocrystal particles. The band gap is a function of the size of the nanocrystal particle. As a result of the narrow size distribution of the capped nanocrystal particles, the illuminated nanocrystal particles emit light of a narrow spectral range resulting in high purity light. Spectral emissions in a narrow range of no greater than about 60 nm, preferably no greater than about 40 nm and most preferably no greater than about 30 nm at full width half max (FWHM) are observed. Spectral emissions in even narrower ranges are most preferred.

The nanocrystal particles are preferably passivated or capped either with organic or inorganic passivating agents to eliminate energy levels at the surface of the crystalline material that lie within the energetically forbidden gap of the bulk interior. These surface energy states act as traps for electrons and holes that would normally degrade the luminescence properties of the material. Such passivation produces an atomically abrupt increase in the chemical potential at the interface of the semiconductor and passivating layer (Alivisatos, *J. Phys. Chem.* 100:13226 (1996), which is hereby incorporated by reference in its entirety). As a result, higher quantum efficiencies can be achieved.

Exemplary capping agents include organic moieties such as tri-n-octyl phosphine (TOP) and tri-n-octyl phosphine oxide (TOPO) (Murray et al., *J. Am. Chem. Soc.* 115:8706 (1993); Kuno et al., *J. Phys. Chem.* 106(23):9869 (1997), each of which is hereby incorporated by reference in its entirety), as well as inorganic moieties such as CdS-capped CdSe and the inverse structure (Than et al., *J. Phys. Chem.* 100:8927 (1996), which is hereby incorporated by reference in its entirety), ZnS grown on CdS (Youn et al., *J. Phys. Chem.* 92:6320 (1988), which is hereby incorporated by reference in its entirety), ZnS on CdSe and the inverse structure (Kortan et al., *J. Am. Chem. Soc.* 112:1327 (1990); Hines et al., *J. Phys. Chem.* 100:468 (1996), each of which is hereby incorporated by reference in its entirety), ZnSe-capped CdSe nanocrystals (Danek et al., *Chem. Materials* 8:173 (1996), which is hereby incorporated by reference in its entirety), and $SiO_2$ on Si (Wilson et al., *Science* 262:1242 (1993), which is hereby incorporated by reference in its entirety).

In general, particles passivated with an inorganic coating are more robust than organically passivated particles and have greater tolerance to processing conditions used for their incorporation into devices. Particles that include a "core" of one or more first semiconductor materials can be surrounded by a "shell" of a second semiconductor material.

Thus, the nanocrystal particles as used in the present invention can be formed of one or more semiconducting materials. Suitable semiconducting materials include, without limitation, a group IV material alone (e.g., Si and Ge), a combination of a group IV material and a group VI material, a combination of a group III material and a group V material, or a group II material and a group VI material. When a combination of materials are used, the semiconducting materials are presented in a "core/shell" arrangement.

Suitable core/shell material combinations include, without limitation, group IV material forming the core and group VI materials forming the shell; group III material forming the core and group V materials forming the shell; and group II material forming the core and group VI materials forming the shell. Exemplary core/shell combinations for groups IV/VI are: Pb and one or more of S, Se, and Te. Exemplary core/shell combinations for groups III/V are: one or more of Ga, In, and Al as the group III material and one or more of N, P, As, and Sb as the group V material. Exemplary core/shell combinations for groups II/VI are: one or more of Cd, Zn, and Hg as the group II material, and one or more of S, Se, and Te as the group VI material. Other combinations now known or hereinafter developed can also be used in the present invention.

Fluorescent emissions of the resulting nanocrystal particles can be controlled based on the selection of materials and controlling the size distribution of the particles. For example, ZnSe and ZnS particles exhibit fluorescent emission in the blue or ultraviolet range (~400 nm or less); CdSe, CdS, and CdTe exhibit fluorescent emission in the visible spectrum (between about 440 and about 700 nm); InAs and GaAs exhibit fluorescent emission in the near infrared range (~1000 nm), and PbS, PbSe, and PbTe exhibit fluorescent emission in the near infrared range (i.e., between about 700-2500 nm). By controlling growth of the nanocrystal particles it is possible to produce particles that will fluoresce at desired wavelengths. As noted above, smaller particles will afford a shift to the blue (higher energies) as compared to larger particles of the same material(s).

Preparation of the nanocrystal particles can be carried out according to known procedures, e.g., Murray et al., *MRS Bulletin* 26(12):985-991 (2001); Murray et al., *IBM J. Res. Dev.* 45(1):47-56 (2001); Sun et al., *J. Appl. Phys.* 85(8, Pt. 2A): 4325-4330 (1999); Peng et al., *J. Am. Chem. Soc.* 124 (13):3343-3353 (2002); Peng et al., *J. Am. Chem. Soc.* 124 (9):2049-2055 (2002); Qu et al., *Nano Lett.* 1(6):333-337 (2001); Peng et al., *Nature* 404(6773):59-61 (2000); Talapin et al., *J. Am. Chem. Soc.* 124(20):5782-5790 (2002); Shevenko et al., *Advanced Materials* 14(4):287-290 (2002); Talapin et al., *Colloids and Surfaces, A: Physiochemical and Engineering Aspects* 202(2-3):145-154 (2002); Talapin et al., *Nano Lett.* 1(4):207-211 (2001), each of which is hereby incorporated by reference in its entirety.

Whether in a core/shell arrangement or otherwise passivated with other compounds, the nanocrystal particles can also be rendered water soluble, if so desired. To make water-soluble nanocrystal particles, hydrophilic capping compounds are bound to the particles. One suitable class includes carboxylic acid capping compounds with a thiol functional group (forming a sulfide bridge with the nanocrystal particle), which can be reacted with the nanocrystal. Exemplary capping compounds include, without limitation, mercaptocarboxylic acid, mercaptofunctionalized amines (e.g., aminoethanethiol-HCl, homocysteine, or 1-amino-2-methyl-2-propanethiol-HCl), mercaptofunctionalized sulfonates, mercaptofunctionalized alkoxides, mercaptofunctionalized phosphates and phosphonates, aminofunctionalized sulfonates, aminofunctionalized alkoxides, aminofunctionalized phosphates and phosphonates, phosphine(oxide)functionalized sulfonates, phosphine(oxide)functionalized alkoxides, phosphine(oxide)functionalized phosphates and phosphonates, and combinations thereof. Procedures for binding these capping compounds to the nanocrystal particles are known in the art, e.g., U.S. Pat. No. 6,319,426 to Bawendi et al., which is hereby incorporated by reference in its entirety.

Attachment of a nanocrystal particle to the opposite end of the nucleic acid probe can be carried out using any of a variety of known techniques, for example, either a terminal base or another base near the terminal base can be bound to the nanocrystal particle. Procedure used for tethering dyes to the nucleic acid can likewise be used to tether the nanocrystal particle thereto. Details on these procedures are described in, e.g., *Bioconjugate Techniques*, Hermanson, ed. (Academic Press) (1996), which is hereby incorporated by reference in its entirety.

Having identified the sequence of a nucleic acid molecule to be used as a probe in a sensor of the present invention, and having selected the appropriate fluorophore and metal nanoparticle film to be utilized, the sensor of the present invention can be assembled using the above-described procedures. Attachment of the fluorophore to one end of the nucleic acid probe can be carried out prior to attachment of the opposite end of the nucleic acid probe to the metal nanoparticle film, or vice versa. Alternatively, the probe can be ordered from any one of various vendors that specialize in preparing oligonucleotides to desired specifications (i.e., having one end modified for binding to the metal nanoparticle film and the other end bound by a fluorophore) and thereafter attached to the metal nanoparticle film. Two exemplary vendors are Midland Certified Reagent Co. (Midland, Tex.) and Integrated DNA Technologies, Inc. (Coralville, Iowa).

In preparing the sensor chips of the present invention, a competitor (or spacer) molecule can also be attached to the metal nanoparticle film, either as a separate step or as a single step (i.e., using a solution containing both the nucleic acid probe and the competitor molecule). The role of the competitor molecule is simply to minimize the concentration (and promote dispersion) of nucleic acid probes bound to the metal nanoparticle film, thereby inhibiting the likelihood of interference between adjacent nucleic acid probes, which could result in background fluorescence. It can also help to inhibit non-specific interaction between the nucleic acid probe and the metal nanoparticles film. Depending on the nature of the metal nanoparticle film, the competitor molecule may not be needed to optimize performance of the sensor device. Use of competitor molecules for some but not all of the spots on a sensor array is also contemplated; this can be used to optimize similar probe loading at each of the spots on the array. Like the nucleic acid probes, the competitor molecule contains a reactive group such as (without limitation) carboxyl, amino, hydroxyl, thiol, or the like, thereby allowing for coupling of the competitor molecule to the metal nanoparticle film. Preferred competitor molecules include, without limitation, thiol-containing compounds, such as mercaptopropanol, cysteine, thiooctic acid, 2-mercaptoethanol, 3-mercapto-2-butanol, 2-mercapto, 1,2-propanediol, 2-(butylamino) ethanethiol, 2-dimethylaminoethanethiol, 2-diethylaminoethanethiol, 3-mercaptopropionic acid, etc.

According to one approach, the metal nanoparticle film is first exposed to a solution containing the competitor molecule and allowed to self-assemble (to the surface) for a sufficient length of time. Thereafter, the modified film is secondly exposed to a solution containing the nucleic acid probe and allowed to self-assemble (to the surface) for a sufficient length of time. As is well known in the art, the exposure time to one or both of the solutions can vary according to the concentrations of the competitor molecule and the nucleic acid probe in their respective solutions. After each exposure, the metal nanoparticle film can be rinsed with pure water or saline solution, preferably at elevated temperatures so as to remove unbound competitor or unbound nucleic acid probe, respectively.

According to another approach, the metal nanoparticle film is simultaneously exposed to a solution containing both the competitor molecule and the nucleic acid probe, and allowed to self-assemble for a sufficient length of time. As noted above, the exposure time to the combined solution can vary according to the concentrations of the competitor molecule and the nucleic acid probe. After exposure, the metal nanoparticle film can be briefly rinsed with pure water or saline solution, preferably at elevated temperatures so as to remove unbound competitor and/or unbound nucleic acid probe. The resulting sensor chip can then be used to detect the presence of target nucleic acid molecules in sample preparations.

The ratio of the competitor molecule to the nucleic acid probe is preferably greater than 1:2, more preferably between about 1:2 and about 1:100, most preferably between about 1:4 and about 1:100. As demonstrated in the Examples, unlike planar gold quenching surfaces, which require the competitor molecule to achieve optimal efficiency of the device, Ag nanoparticles films preferably contain little or no competitor molecule (i.e., where probe concentration exceeds competitor molecule concentration by several fold). Thus, use of the competitor can be an effective approach for equilibrating the potential relative intensity change (R-value) across an array; no two spots on an array would necessarily have to contain the same competitor:probe ratio.

The sensor chip can have a number of configurations depending on the nature and number of target nucleic acid molecules to be identified by a single chip.

According to one embodiment, the sensor chip is constructed using one or more nucleic acid probes, whether the same or different, all of which are directed to the same target molecule (perhaps, however, at different locations on the target). In this case, the probes can be attached to the metal nanoparticle film in any location or over the substantially entire surface thereof.

Figure 2:
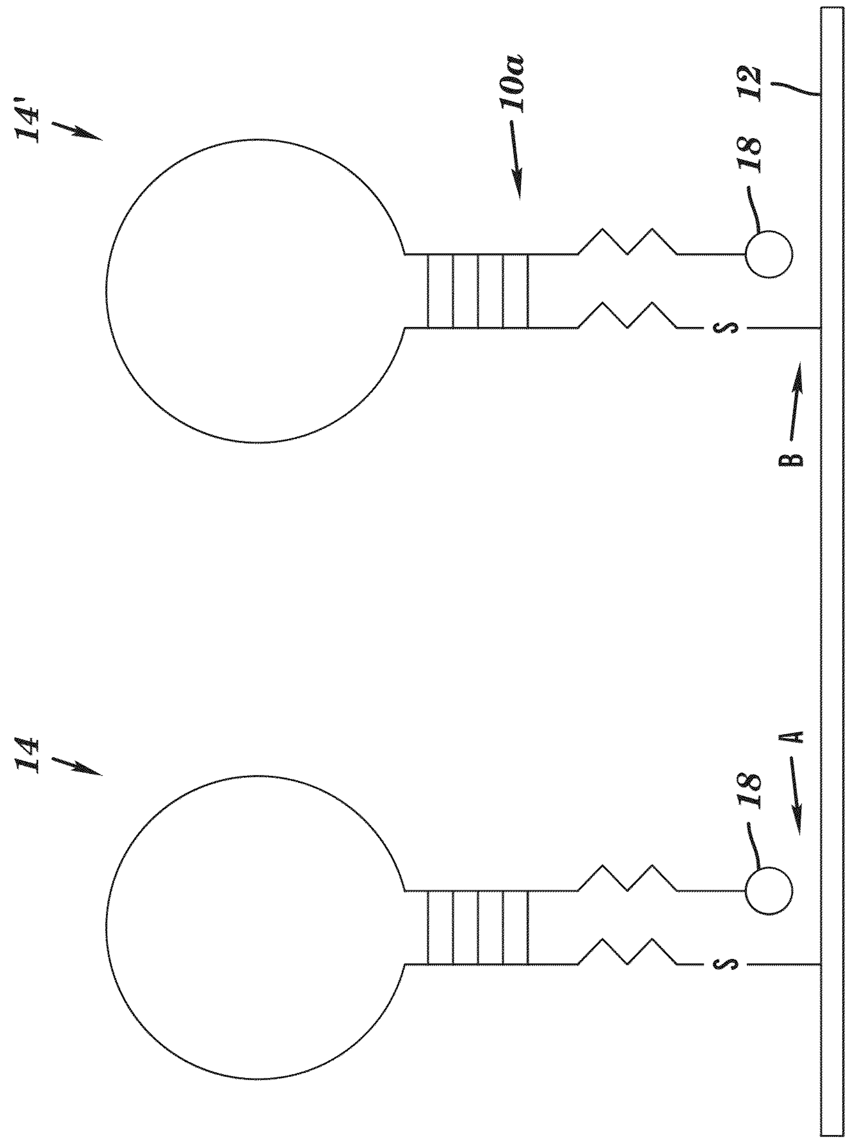
FIG. 2 illustrates one particular embodiment of an arrayed sensor chip, where two or more nucleic acid hairpin probes are bound to the metal nanoparticle film so that they are present in discrete locations, designated A and B. The metal nanoparticle film can be continuous or discontinuous.

According to another embodiment, the sensor chip is prepared as an array containing a plurality of discrete locations or "spots" where the probe molecules are bound to the sensor chip surface. Preferably, a distinct probe is bound to each of the spots. Arrays of this type can be fabricated to contain in excess of $10^2$, $10^3$, $10^4$, or even $10^5$ spots. For example, as shown in FIG. 2, the sensor chip 10*a* is constructed using two or more nucleic acid probes 14,14' each having a different target nucleic acid molecule, where each of the two or more nucleic acid probes 14,14' is localized to a specific region A, B on the metal nanoparticle film (on substrate 12). One probe 14 (and its target) can be distinguished from another probe 14' (and its target) by the localization of any fluorescence emissions from the sensor chip 10*a*. In this arrangement, the fluorophores 18 used on the two or more nucleic acid probes 14,14' can be the same or they can be different.

Figure 3:
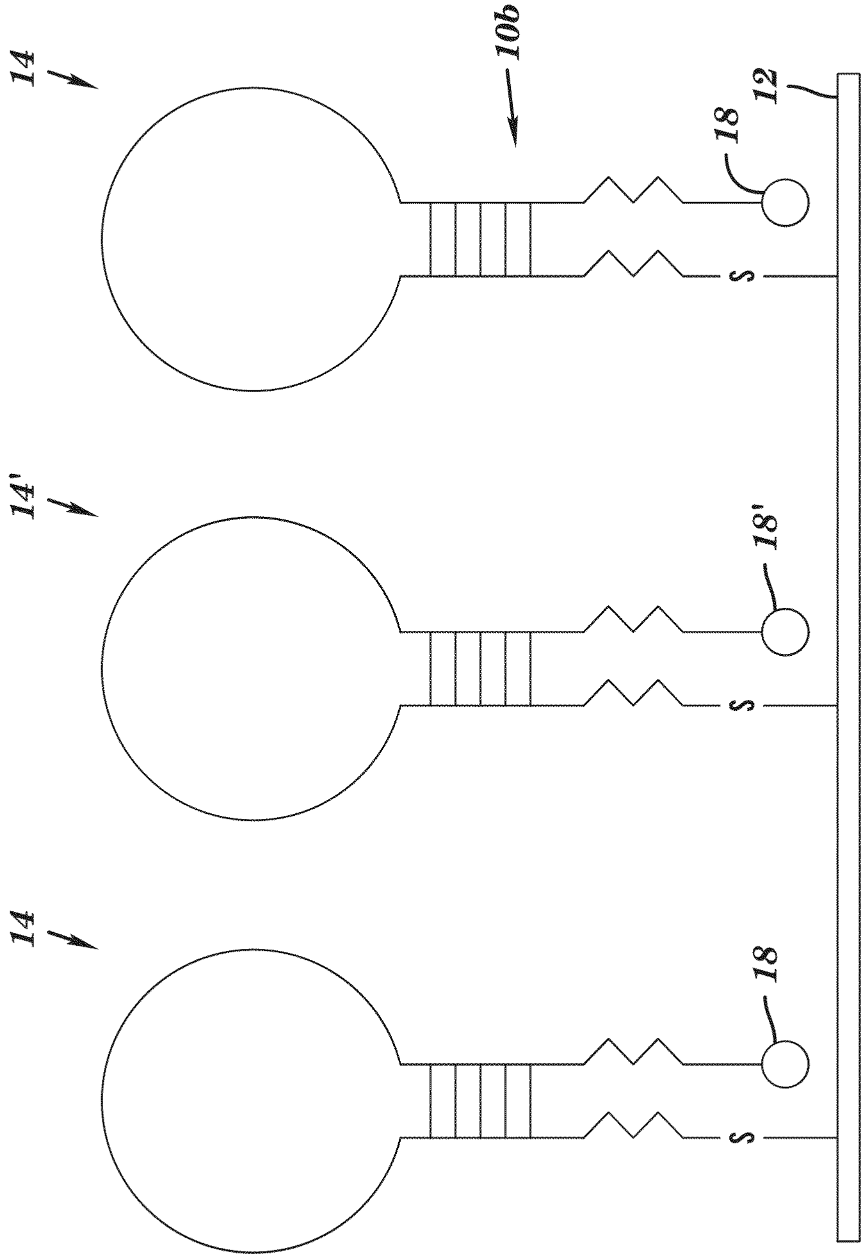
FIG. 3 illustrates another embodiment of the sensor chip, where two or more nucleic acid hairpin probes are bound to the metal nanoparticle film so that they are co-localized. Different fluorophores having distinct fluorescent emissions distinguish one probe from another.

According to another embodiment, shown in FIG. 3, the sensor chip 10*b* is constructed using two or more nucleic acid probes 14,14' each having a different target nucleic acid molecule, where the two or more nucleic acid probes are co-localized (i.e., overlapping locations) on the metal nanoparticle film (substrate 12) or portions thereof. In this arrangement, the fluorophores 18,18' used on the two or more nucleic acid probes are different so that fluorescent emissions from each can be distinguished from any others.

To distinguish between multiple fluorescent emissions emanating from a single location on the surface of the sensor chip (i.e., signal from one probe rather than another), the fluorescent emissions need only differ sufficiently to allow for resolution by the detector being utilized. Resolution of the signals can also depend, in part, on the nature of the emission pattern. For example, narrow emission maxima are more easily resolved than broad emission maxima that may interfere with emissions by other fluorophores. Thus, the selection of fluorophores should be made so as to minimize the interference given the sensitivity of the detector being utilized. By way of example, highly sensitive detectors can discriminate between the narrow emission maxima of semiconductor nanocrystals and dyes, allowing for separation of emission maxima that differ by about 1 nm or greater. Preferably, however, the emission maxima between the two or more fluorophores will differ by about 10 nm or greater or even 20 nm or greater, more preferably 30 nm or greater or even 40 nm or greater. Generally, the greater the separation between the emission maxima of the two or more fluorophores, the easier it will be to resolve their signals from overlapping locations on the surface of the sensor chip.

The sensor chip is intended to be used as a component in a biological sensor device or system. Basically, the device includes, in addition to the sensor chip, a light source that illuminates the sensor chip at a wavelength suitable to induce fluorescent emissions by the fluorophores associated with the one or more probes bound to the chip, and a detector positioned to capture any fluorescent emissions by the fluorophores.

The light source can be any light source that is capable of inducing fluorescent emissions by the selected fluorophores. Light sources that provide illumination wavelengths between about 200 nm and about 2000 nm are preferred. Exemplary light sources include, without limitation, lasers and arc lamps. Typical powers for lasers are at least about 1 mW; however, when used with an objective lens focusing the laser light to a small spot, as little as about 1 μW is sufficient. By way of example, Xenon arc lamps should be at least about 75 W.

The detector can be any detection device that is capable of receiving fluorescent emissions and generating a response to be examined by an operator of the biological sensor device. Suitable detectors include, without limitation, charge coupled devices (CCDs), photomultiplier tubes (PMTs), avalanche photodiodes (APDs), and photodiodes that contain a semiconductor material such as Si, InGaAs, extended InGaAs, Ge, HgCdTe, PbS, PbSe, or GaAs to convert optical photons into electrical current. Of these suitable detectors, the CCD is preferred because it can produce an image in extremely dim light, and its resolution (i.e., sharpness or data density) does not degrade in low light.

In addition to the above components, the biological sensor device can also include a notch filter positioned between the light source and the sensor chip and/or a bandpass filter positioned between the sensor chip and the detector. The notch filter will screen out a narrow band of photoradiation, i.e., at or near the excitation maxima of the selected fluorophore(s), so as to minimize any background excitation by materials present in or on the sensor chip or by non-quenched fluorophore(s). The bandpass filters control the spectral composition of transmitted energy, typically though not exclusively by the effects of interference, resulting in high transmission over narrow spectral bands. By way of example, the bandpass filter can allow passage of light within a range that is not more than about 10 nm greater or less than the wavelength of the maximum emissions of the fluorophore(s). When two or more fluorophores are used having different emission maxima, the bandpass filter will emit passage of light within a larger wavelength band that extends from slightly below than the lowest wavelength maxima up to slightly higher than the highest wavelength maxima. Alternatively, when multiple fluorophores are used the emission signal can be split prior to passage through any filters (i.e., one for each fluorophore). Each split emission signal can include a separate bandpass filter that is configured for the emission maxima of one fluorophore but not the others.

Figure 4:
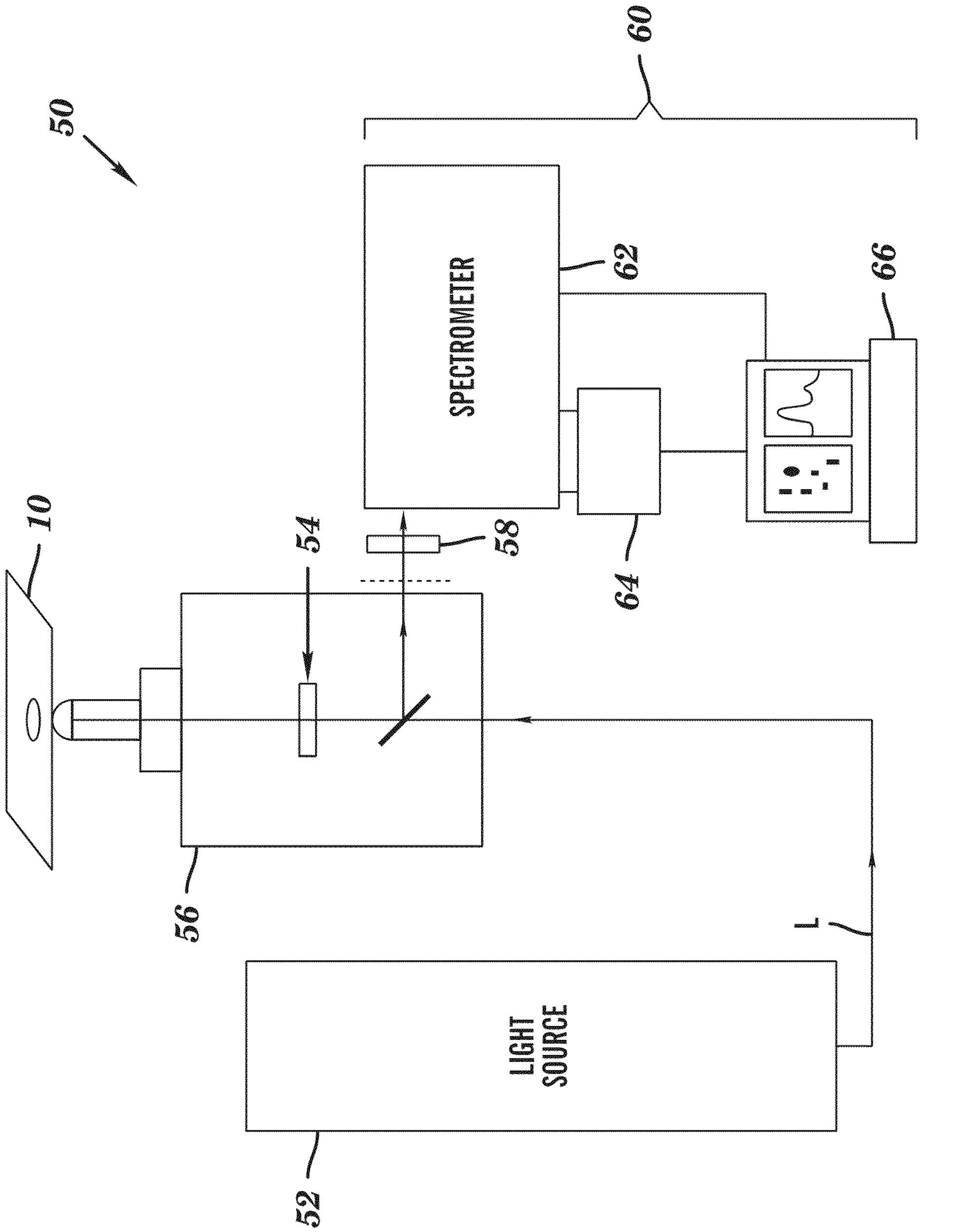
FIG. 4 is a schematic showing a biological detection device according to one embodiment of the present invention, which includes, inter alia, an inverted fluorescence microscope equipped with a liquid nitrogen cooled charge coupled device (CCD).

By way of example, FIG. 4 shows the configuration of one particular embodiment of the biological sensor device 50. The device includes a light source 52 that produces a focused beam of light L which is directed through a notch filter 54 and through an inverted microscope 56 (as shown, the notch filter is a component of the inverted microscope), where it contacts the sensor chip 10 placed on a sample stage. Any fluorescent emissions are captured by the inverted microscope 56 and the signal passes through a bandpass filter 58 prior to reaching the detector device 60. As shown, the detector device 60 includes a spectrophotometer 62 coupled to a CCD 64, whose electrical output signal is directed to a computer 66 or similar device capable of receiving the electrical output and generating an image of the detected fluorescence emitted from the sensor chip 10.

Figure 5:
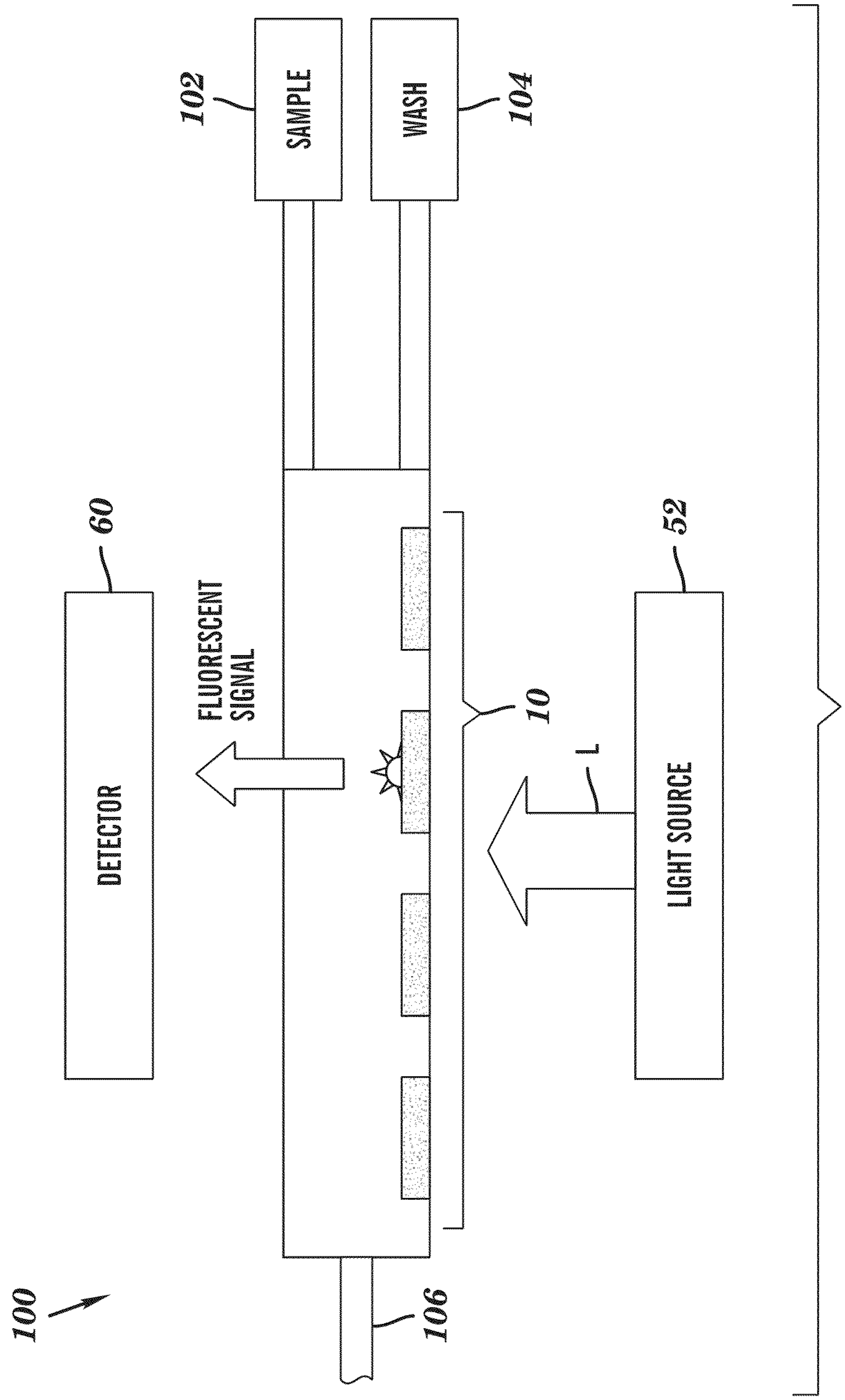
FIG. 5 is a schematic showing a flow-through cell that incorporates a sensor chip having a light transmissive, metal nanoparticles surface functionalized with the hairpin probes. Because of the light transmissive property of the metal nanoparticle film the light source and detector can be positioned on opposite sides of the flow cell. As shown, the light source is below the flow-through cell and the detector above; however, the opposite arrangement can also be utilized.
Figure 6A:
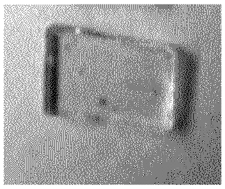
FIGS. 6A-G show the images of the Ag substrates fabricated under different Ag exposure times: (6A) 10 min, (6B) 20 min, (6C) 30 min, (6D) 1 hr, (6E) 2 hr, (6F) 3 hr, and (6G) 4 hr.
Figure 6B:
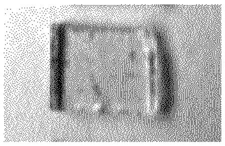
Figure 6C:
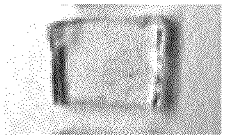
Figure 6D:
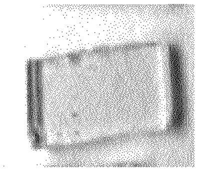
Figure 6E:
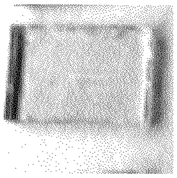
Figure 6F:
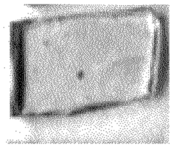
Figure 6G:
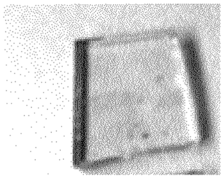

FIG. 5 shows schematically a flow-through cell 100 of the present invention, which includes the sensor chip 10 forming a portion of the flow-through cell. The flow-through cell 100 is preferably a microfluidic device that includes one or more inlets in fluid communication with a sample source 102 and a wash fluid source 104. Fluid that flows over the sensor chip (with or without a dwell time) can be removed via outlet 106. Because the metal nanoparticle film is light transmissive, the illumining light L can be directed through one side (bottom, as shown) of the cell and the detected fluorescent signal can be measured by the detector 60 on the other side of the cell. Any suitable optical set-up (bandpass filter, etc.) can be used to remove the illuminating light L from interfering with the detector.

The sample is preferably present in the form of a buffered solution or other medium suitable for use during hybridization. The sample itself can be either a clinical or environmental sample to which buffer or buffer salts are added, derived from purification of DNA or RNA from clinical or environmental specimens, or the product of a PCR reaction, etc. Basically, the sample can be in any form where the suspected nucleic acid target is maintained in a substantially stable manner (i.e., without significant degradation).

During use of the biological sensor device and the associated sensor chip, the presence of a target nucleic acid molecule in a sample can be achieved by first exposing the sensor chip to a sample under conditions effective to allow any target nucleic acid molecule in the sample to hybridize to the first and/or second regions of the nucleic acid probe(s) present on the sensor chip, illuminating the sensor chip with light sufficient to cause emission of fluorescence by the fluorophore(s), i.e., associated with the nucleic acid probe(s), and then determining whether or not the sensor chip emit(s) detectable fluorescent emission (of the fluorophore(s)) upon said illuminating. When fluorescent emission by the fluorophore(s) is detected from the chip, such detection indicates that the nucleic acid probe is in the non-hairpin conformation and therefore that the target nucleic acid molecule is present in the sample.

The conditions utilized during the exposure step include hybridization and then wash conditions, as is typical during hybridization procedures. The hybridization and wash conditions can be carried in buffered saline solutions either at or slightly above room temperature (i.e., up to about 30° C.). Alternatively, as is known in the art, the hybridization conditions can be selected so that stringency will vary. That is, lower stringency conditions will discriminate less between perfectly matched target nucleic acid molecules and non-perfectly matched nucleic acid molecules, whereas higher stringency conditions will discriminate between perfectly matched and non-perfectly matched nucleic acid molecules. In general, the highest stringency that can be tolerated by the probe and the intended target can be selected so as to minimize or completely avoid the possibility of a false positive response caused by hybridization to non-perfectly matched nucleic acid molecules. Detection performance can also be enhanced with the utility of a flow-through cell device by alleviating the rate-limited reaction. A flow-through device can increase the likelihood of the collision between the probe and target DNA at the reaction site due to the confined space and also the fluidic flow. Alternatively, it may be desirable to begin hybridization at a temperature above the melting temperature of the hairpin probe, thus promoting an open conformation, and then during the course of the hybridization procedure allowing the chip to cool so that hairpins not participating in hybridization (i.e., in cases where there is no complementarity) to re-fold, and fluorescence to be quenched. The latter procedure would be desirable, for example, when the hairpin probe is quite stable (having a predicted E value in the range of about −9 to about −12 kcal/mol), even in the presence of target nucleic acid molecules. In either case though, detection typically is not carried out until the hybridization and wash procedures have been completed.

An example of suitable stringency conditions is when hybridization is carried out at a temperature of at least about 35° C. using a hybridization medium that includes about 0.3M $Na^+$, followed by washing at a temperature of at least about 35° C. with a buffer that includes about 0.3M $Na^+$ or less. Higher stringency can readily be attained by increasing the temperature for either hybridization or washing conditions or decreasing the sodium concentration of the hybridization or wash medium. Other factors that affect the melting temperature of the hairpin probe include its GC content and the length of the stem (and whether the stem perfectly hybridizes intramolecularly). Nonspecific binding may also be controlled using any one of a number of known techniques such as, for example, addition of heterologous RNA, DNA, and SDS to the hybridization buffer, treatment with RNase, etc. Wash conditions can be performed at or below stringency of the hybridization procedure, or even at higher stringency when so desired. Exemplary high stringency conditions include carrying out hybridization at a temperature of about 50° C. to about 65° C. (from about 1 hour up to about 12 hours) in a hybridization medium containing 2×SSC buffer (or its equivalent), followed by washing carried out at between about 50° C. to about 65° C. in a 0.1×SSC buffer (or its equivalent). Variations on the hybridization conditions can be carried out as described in Sambrook et al., *Molecular Cloning: A Laboratory Manual*, Second Edition, Cold Spring Harbor Press, NY (1989), which is hereby incorporated by reference in its entirety.

The nucleic acid probes, used in preparing sensor chips of the present invention, can be selected so that they hybridize to target nucleic acid molecules that are specific to pathogens, are associated with disease states or conditions, contain polymorphisms that may or may not be associated with a disease state but can also be a forensic target or associated with a breeding trait for plants or animal. Other uses should be appreciated by those of ordinary skill in the art.

Pathogens that can be identified using the products and processes of the present invention include any bacteria, fungi, viruses, rickettsiae, chlamydiae, and parasites, but preferably those identified as belonging within the classifications listed as Biosafety Levels Two, Three, and Four by the U.S. Centers for Disease Control and Prevention, the National Institutes of Health, and the World Health Organization.

Exemplary bacterial pathogen that can be identified in accordance with the present invention include, without limitation: *Acinetobacter calcoaceticus, Actinobacillus* species (all species), *Aeromonas hydrophila, Amycolata autotrophica, Arizona hinshawii* (all serotypes), *Bacillus anthracis, Bartonella* species (all species), *Brucella* species (all species), *Bordetella* species (all species), *Borrelia* species (e.g., *B. recurrentis, B. vincenti*), *Campylobacter* species (e.g., *C. fetus, C. jejuni*), *Chlamydia* species (e.g., *Chl. psittaci, Chl. trachomatis*), *Clostridium* species (e.g., *Cl. botulinum, Cl. chauvoei, Cl. haemolyticum, Cl. histolyticum, Cl. novyi, Cl. septicum, Cl. tetani*), *Corynebacterium* species (e.g., *C. diphtheriae, C. equi, C. haemolyticum, C. pseudotuberculosis, C. pyogenes, C. renale*), *Dermatophilus congolensis, Edwardsiella tarda, Erysipelothrix insidiosa, Escherichia coli* (e.g., all enteropathogenic, enterotoxigenic, enteroinvasive and strains bearing K1 antigen), *Francisella tularensis, Haemophilus* species (e.g., *H. ducreyi, H. influenzae*), *Klebsiella* species (all species), *Legionella pneumophila, Leptospira* interrogans (e.g., all serotypes), *Listeria* species (all species), *Moraxella* species (all species), *Mycobacteria* species (all species), *Mycobacterium avium, Mycoplasma* species (all species), *Neisseria* species (e.g., *N. gonorrhoea, N. meningitides*), *Nocardia* species (e.g., *N. asteroides, N. brasiliensis, N. otitidiscaviarum, N. transvalensis*), *Pasteurella* species (all species), *Pseudomonas* species (e.g., *Ps. mallei, Ps. pseudomallei*), *Rhodococcus equi, Salmonella* species (all species), *Shigella* species (all species), *Sphaerophorus necrophorus, Staphylococcus aureus, Streptobacillus moniliformis, Streptococcus* species (e.g., *S. pneumoniae, S. pyogenes*) and particularly methicillin-resistant species of *Streptococcus, Treponema* species (e.g., *T. carateum, T. pallidum*, and *T. pertenue*), *Vibrio* species (e.g., *V. cholerae, V. parahemolyticus*), and *Yersinia* species (e.g., *Y. enterocolitica, Y. pestis*).

Exemplary fungal pathogens that can be identified in accordance with the present invention include, without limitation: *Blastomyces dermatitidis, Cryptococcus neoformans, Paracoccidioides braziliensis, Trypanosoma cruzi, Coccidioides immitis, Pneumocystis carinii*, and *Histoplasma* species (e.g., *H. capsulatum, H. capsulatum* var. *duboisii*).

Exemplary parasitic pathogens that can be identified in accordance with the present invention include, without limitation: *Endamoeba histolytica, Leishmania* species (all species), *Naegleria gruberi, Schistosoma mansoni, Toxocara canis, Toxoplasma gondii, Trichinella spiralis*, and *Trypanosoma cruzi*.

Exemplary viral, rickettsial, and chlamydial pathogens that can be identified in accordance with the present invention include, without limitation: Adenoviruses (all types), Cache Valley virus, Coronaviruses, Coxsackie A and B viruses, Cytomegaloviruses, Echoviruses (all types), Encephalomyocarditis virus (EMC), Flanders virus, Hart Park virus, Hepatitis viruses-associated antigen material, Herpesviruses (all types), Influenza viruses (all types), Langat virus, Lymphogranuloma venereum agent, Measles virus, Mumps virus, Parainfluenza virus (all types), Polioviruses (all types), Poxviruses (all types), Rabies virus (all strains), Reoviruses (all types), Respiratory syncytial virus, Rhinoviruses (all types), Rubella virus, Simian viruses (all types), Sindbis virus, Tensaw virus, Turlock virus, Vaccinia virus, Varicella virus, Vesicular stomatitis virus, Vole rickettsia, Yellow fever virus, Avian leukosis virus, Bovine leukemia virus, Bovine papilloma virus, Chick-embryo-lethal orphan (CELO) virus or fowl adenovirus 1, Dog sarcoma virus, Guinea pig herpes virus, Lucke (Frog) virus, Hamster leukemia virus, Marek's disease virus, Mason-Pfizer monkey virus, Mouse mammary tumor virus, Murine leukemia virus, Murine sarcoma virus, Polyoma virus, Rat leukemia virus, Rous sarcoma virus, Shope fibroma virus, Shope papilloma virus, Simian virus 40 (SV-40), Epstein-Barr virus (EBV), Feline leukemia virus (FeLV), Feline sarcoma virus (FeSV), Gibbon leukemia virus (GaLV), Herpesvirus (HV) ateles, Herpesvirus (HV) saimiri, Simian sarcoma virus (SSV)-1, Yaba, Monkey pox virus, Arboviruses (all strains), Dengue virus, Lymphocytic choriomeningitis virus (LCM), *Rickettsia* (all species), Yellow fever virus, Ebola fever virus, Hemorrhagic fever agents (e.g., Crimean hemorrhagic fever, (Congo), Junin, and Machupo viruses, Herpesvirus simiae (Monkey B virus), Lassa virus, Marburg virus, Tick-borne encephalitis virus complex (e.g., Russian spring-summer encephalitis, Kyasanur forest disease, Omsk hemorrhagic fever, and Central European encephalitis viruses), and Venezuelan equine encephalitis virus.

Thus, a further aspect of the present invention relates to a method of detecting presence of a pathogen in a sample that is carried out by performing the above-described method (of detecting the presence of the target nucleic acid molecule) when using a sensor chip having a nucleic acid probe with at least portions of the first and/or second region thereof specific for hybridization with a target nucleic acid molecule of a pathogen.

Yet another aspect of the present invention relates to a method of genetic screening that is carried out by performing the above-described method (of detecting the presence of the target nucleic acid molecule) when using a sensor chip having a nucleic acid probe with at least portions of the first and/or second region thereof specific for hybridization with a genetic marker. As noted above, the genetic marker can be associated with disease states or conditions, contain polymorphisms that may or may not be associated with a disease state but can also be a forensic target or associated with a breeding trait for plants or animal.

EXAMPLES

The following examples are provided to illustrate embodiments of the present invention but are by no means intended to limit its scope.

Example 1

Fabrication and Characterization of Nanostructured Ag Substrates

Fabrication of nanostructured Ag substrates was accomplished by covalently attaching Ag nanoparticles onto 3-mercaptopropyl-trimethoxysilane (MPTS, Gelest, Inc) treated glass chips via $Ag^+$ ion reduction in N—N dimethylformamide (DMF, Mallinckrodt) (Pastoriza-Santos et al., *Langmuir* 15:948-951 (1999); Pastoriza-Santos et al., *J. Colloid Interface Sci.* 221:236-241 (2000); Sabanayagam et al., *Nucleic Acids Res.* 35(2):e13 (2007), each of which is hereby incorporated by reference in its entirety. First, a standard glass microscope slide was cleaned by soaking with piranha solution ($H_2SO_4$: 35%: $H_2O_2$; 3:1) for 15 minutes. The glass slide was then rinsed with distilled, deionized (DDI) water, soaked in a 10 M NaOH solution for 5 minutes, rinsed again with DDI water, and finally dried under nitrogen gas. The cleaned glass slides were silanized by incubating in a solution composed of 1% MPTS, 95% methanol, and 4% 1 mM acetic acid for 30 minutes. The silanized glass slides were then sonicated (300-watt Vibra-cell™ probe sonicator, Sonic & Material Inc.) in a 95% ethanol and 5% water solution for 2 minutes and dried under nitrogen gas. Coating of the silanized glass slides with Ag nanoparticles was accomplished by incubating them in a solution of 10 mM $AgNO_3$ in DMF. Lastly, the slides were washed after Ag exposure by sonicating in a 95% ethanol and 5% water solution for 4 minutes, and then dried under nitrogen gas. The Ag substrates were stored at room temperature until needed for DNA attachment experiments.

To examine the effect of Ag NP size and surface coverage on the detection performance, the Ag exposure times were varied from 10 min to 18 hr (10 min, 20 min, 30 min, 1 hr, 2 hr, 3 hr, 4 hr, 8 hr, and 18 hr). A variation in Ag exposure time was anticipated to modulate the nanoparticle size as suggested by Pastoriza-Santos et al (*J. Colloid Interface Sci.* 221:236-241 (2000), which is hereby incorporated by reference in its entirety). FIG. 6 shows an image of the Ag substrates fabricated under different Ag exposure times. Low Ag exposure substrates (10 min, 20 min, 30 min, and 1 hr) were essentially indistinguishable from bare glass, while higher Ag exposure substrates (2 hr, 3 hr and 4 hr) developed a yellow tinted appearance. As discussed below, it was determined that the low Ag exposure substrates had sufficient Ag NPs to support DNA detection despite their transparent appearance (due to a low quantity of Ag NPs that were deposited on the substrate surface). This should allow for novel instrument or device configurations, such as flow-through devices illustrated in FIG. 5, in which imaging or illumination occurs from the opposite face from the functionalized Ag.

Figure 7:
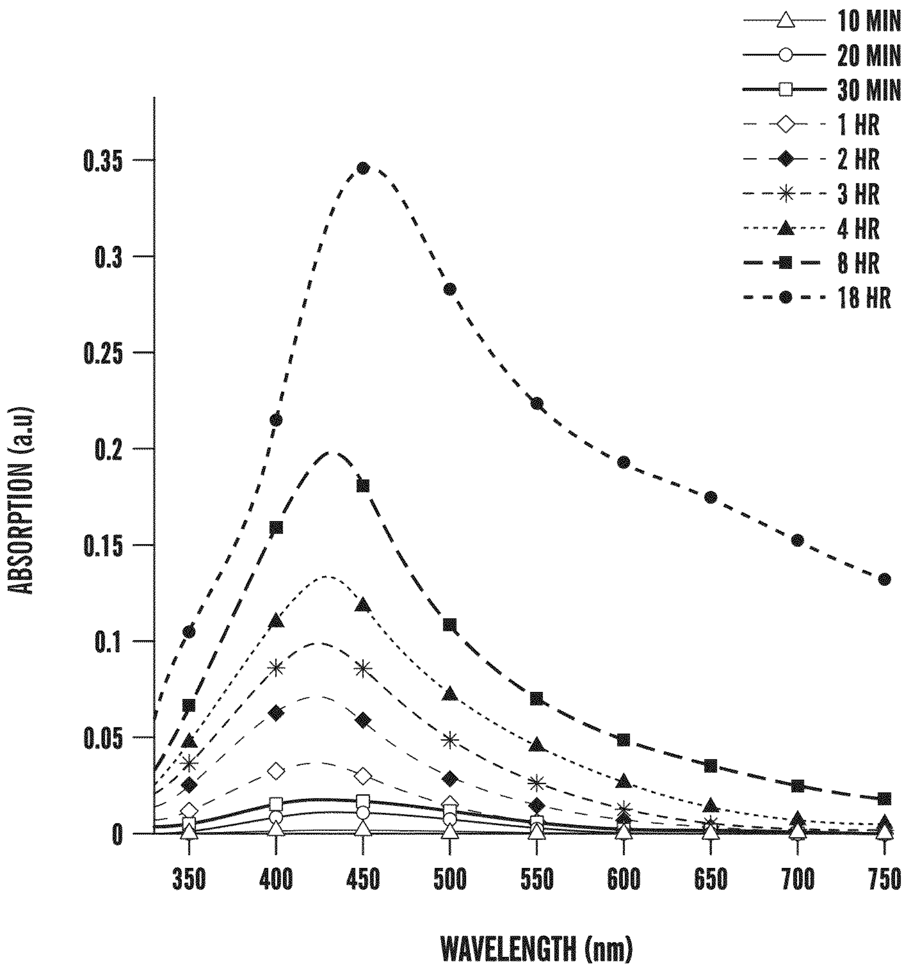
FIG. 7 shows the absorption spectra of Ag substrates prepared with different Ag exposure times in a 10 mM $AgNO_3$ solution in DMF (10 min, 20 min, 30 min, 1 hr, 2 hr, 3 hr, 4 hr, 8 hr, and 18 hr).
Figure 8A:
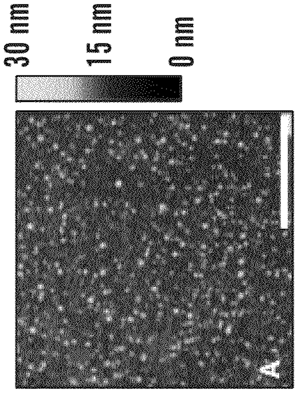
FIGS. 8A-D show atomic force microscopy ("AFM") images showing topographic features of the nanostructured Ag substrates prepared in a 10 mM $AgNO_3$ solution with different Ag exposure times: (8A) 10 min, (8B) 20 min, (8C) 8 hr, and (8D) 18 hr. Scale bar: 400 nm.
Figure 8B:
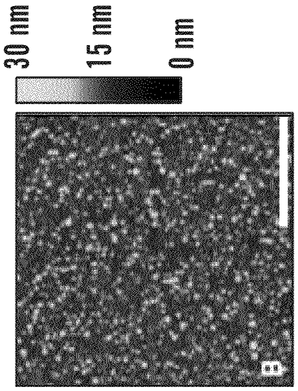
Figure 8C:
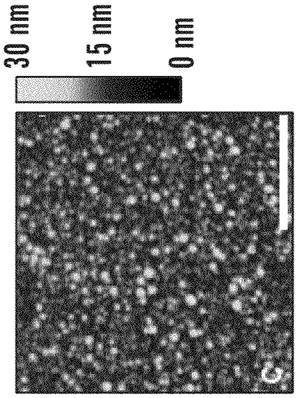
Figure 8D:
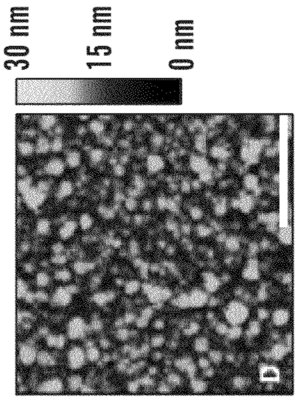

FIG. 7 shows the absorption spectra (Perkin Elmer Lambda 950 UV/Vis) of the Ag substrates prepared with different Ag exposure times ranging from 10 min to 18 hr. The spectra demonstrate a characteristic absorption peak centered at ~420 nm for a 1 hr exposure time. This absorption peak red-shifts from ~420 to 450 nm with increasing Ag exposure time. The absorption magnitude also increased with Ag exposure time as a result of an increase in the amount of Ag NPs that were deposited on the substrates.

To obtain a more detailed understanding of the nanostructured Ag surfaces, the surface topography was examined by atomic force microscopy (AFM). AFM topography images of the Ag substrates were obtained using a Digital Instruments Nanoscope IIIa operated in tapping mode using a Si tip (300 kHz, 40 N/m). NP height measurements were made offline using Digital Instruments Software. FIG. 8 shows the AFM images of the Ag substrates prepared in a 10 mM $AgNO_3$ solution with incubation times of 10 min, 20 min, 8 hr, and 18 hr. A lower population density and smaller particle diameter range (~8 to 15 nm) was measured for the 10 min Ag exposed substrates. This is in stark contrast to the 8 hr Ag exposed substrates, where a higher level of NP coverage and wider range of NP diameters (~9 to 50 nm) were observed. The relationship between exposure time, average particle size, particle size range, and particle density is shown in Table 1 in Example 2 below.

Example 2

DNA Detection System Utilizing Nanostructured Ag Substrates as the Sensing Substrates To examine the correlation between the relative intensity change and the substrate surface characterization, the detection performance on nanostructured Ag substrates fabricated under different Ag exposure times in a 10 mM $AgNO_3$ solution was examined.

This experiment employed the previously described probe designated BaPag 1208, which has the nucleotide sequence 5'-TCGTTAGTGTTAGGAAAAAATCAAA-CACTCGCGA-3' (SEQ ID NO: 1). The probe was purchased from Integrated DNA Technologies, Inc (IDT); this probe bears a 3'-tetramethyl rhodamine (TMR) fluorophore ($Ab_{max}$: 559 nm, $Em_{max}$: 583 nm) and a 5'-thiol (disulfide form)). This probe has a secondary structure as described in U.S. Patent Publ. No. 20070166731, which is hereby incorporated by reference in its entirety. Use of this probe permitted the comparison of Ag NP substrate results with prior experiments where planar Au films were used as the sensing substrates (Strohsahl et al., *Nat. Protoc.* 2:2105-2110 (2007), which is hereby incorporated by reference in its entirety). The target DNA molecule, also purchased from Integrated DNA Technologies, Inc., has the sequence 5'-TCGCGAGT-GTTTGATTTTTTCCTAACACTAACGA-3' (SEQ ID NO: 2).

Self assembly was accomplished by incubating each substrate in a solution consisting of 300 nM probe DNA and 300 nM mercaptopropanol (MP) in buffered saline (500 mM NaCl, 20 mM Cacodylic acid, and 0.5 mM ethylenediaminetetraacetic acid (EDTA), pH=7.0) at room temperature for 2 hours (FIG. 5(B)). Next, non-specifically bound DNA probes were removed by washing the substrates with boiling DDI water for 30 seconds. They were then air dried and finally kept in the dark at room temperature for 45 minutes. Hairpin formation was promoted by adding buffered saline to the dried substrates and then soaking them in the dark at room temperature for 45 minutes. Pre-hybridization fluorescence measurements were made for each substrate after removal from the saline solution. Finally, the Ag substrates were immersed in a 2.5 μM label-free target DNA solution overnight. Hybridization to the target DNA, which forces the hairpin probe to open and remove the TMR probe from the proximity of the substrate, was detected by measurement of TMR probe fluorescence.

Figure 9A:
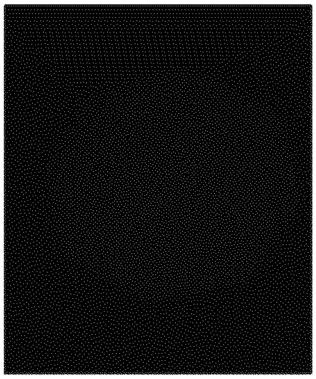
FIGS. 9A-B shows the fluorescence images of TMR-DNA on a nanostructured Ag substrate (20 min Ag exposure), before (9A; average intensity=~3000 (a.u.)) and after (9B; average intensity=~45000 (a.u.)) addition of target DNA. A 14-fold increase in intensity was observed after hybridization. CCD integration time: 1 second.
Figure 9B:
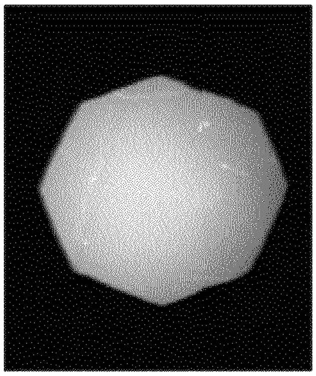

Fluorescence measurements were performed using a system of the type illustrated in FIG. 4, including an Olympus BX-60 fluorescence microscope equipped with a thermoelectrically (TE) cooled charge coupled device (CCD). Samples were excited with incident light from a Hg lamp (100-watt), which was filtered with appropriate optical filter (531±20 nm), reflected by a dichroic mirror, and guided through a 10× objective lens. The emitted light was collected by the cooled CCD after being directed from the sample, through the objective, the dichroic mirror and a bandpass filter (593±20 nm). Fluorescence images were analyzed using Image J software (available online from NCBI). Representative fluorescence images captured using TMR-DNA on a Ag substrate before and after the addition of target DNA are shown in FIGS. 9A-B. The images demonstrate a uniform fluorescence signal across the substrate surface.

The intensity of the fluorescence images shown in FIG. 9A-B increased from baseline intensity of ~3000 to ~45000 a.u. for the pre- and post-hybridized TMR-DNA samples, respectively. To gain a more quantitative understanding of the intensity change from pre- to post-hybridization, the relative intensity change (R-value) was calculated according to Equation 1:

$$R\text{-value}=[(I_{post}-I_{blank})/(I_{pre}-I_{blank})] \quad \text{(Eq. 1)}$$

where $I_{post}$ and $I_{pre}$ represent the post- and pre-hybridization intensity, respectively, and $I_{blank}$ represents the intensity measured with unfunctionalized Ag substrates in buffered saline. For the experiment shown in FIG. 9, the R-value was equal to a 14-fold increase in fluorescence intensity. In contrast, an unfunctionalized glass slide as the sensing substrate provided no fluorescence change (R-value=0).

TABLE 1

Surface Characterization of Nanostructured Ag Substrates and Calculated R-value

| Exposure Time | Particle Size (nm) | Size Range (nm) | Particle Density (per μm²) | Roughness (nm) | R-value* |
|---|---|---|---|---|---|
| Control | | | | 0.58 | |
| 10 min | 4.9 ± 0.9 | 3.6-10 | 315 | 0.84 | 6.6 |
| 20 min | 5.1 ± 1.1 | 3.7-11 | 589 | 1.20 | 14.1 |
| 30 min | 5.4 ± 1.7 | 3.6-29.3 | 722 | 1.57 | 12.0 |

TABLE 1-continued

Surface Characterization of Nanostructured Ag Substrates and Calculated R-value

| Exposure Time | Particle Size (nm) | Size Range (nm) | Particle Density (per μm²) | Roughness (nm) | R-value* |
|---|---|---|---|---|---|
| 1 hour | 6.3 ± 2.3 | 3.8-17.84 | 710 | 1.97 | 11.5 |
| 2 hours | 6.93 ± 2.5 | 3.7-15.6 | 587 | 2.45 | 8.7 |
| 3 hours | 5.9 ± 2.4 | 3.7-27 | 709 | 2.99 | 6.1 |
| 4 hours | 6.752 ± 2.9 | 3.7-31.4 | 720 | 2.50 | 3.4 |

*R-value calculated according to Eq. 1.

In general, higher Ag exposure time yielded higher Ag particle size and substrate surface roughness. The quenching efficiency and R-value are sensitive to the substrate surface roughness, with optimal R-value under these conditions (where [MP]:[DNA]=1:1) being achieved with substrate surface roughness ranges from about 1.20 nm to about 2.00 nm. In contrast, high surface roughness (>3 nm) gives poor quenching and hence R-value under these conditions.

A comparison of the CCD integration times and measured intensities in previous experiments using planar Au substrate (Du et al., *J. Am. Chem. Soc.* 125:4012-4013 (2005), which is hereby incorporated by reference in its entirety) confirmed that the nanostructured Ag substrate provided a surprisingly dramatic (~10-fold) fluorescence enhancement over the planar Au substrate. However, it could be argued that the intensity enhancement was due to an increase in surface area from the nanostructured surface, which increased the number of DNA bounded fluorophores that are attached onto the substrate surface. To answer this question, the surface area of the nanostructured Ag substrate (20 min Ag exposure time) that was available for DNA attachment was calculated. Rather than using the range and mean diameter obtained from the AFM software (see Table 1), values were calculated by measuring the particle size by pixel numbers and comparing that to the scale bar. The apparent diameter of the Ag NPs prepared with 20 minutes of Ag exposure time spanned from 10 to 25 nm, with a mean of 15 nm. A particle density of approximately 589 particles/μm², as measured by AFM, was also used in the calculation. The surface area was calculated based on an assumption of spherical particles.

The surface area of the nanostructured Ag substrate on a 1 μm² glass slide was roughly 0.42 μm², which corresponded to ~42% of the surface area from a planar Au substrate (in reality, the available surface area was even less, given that part of each particle is in contact with the glass surface and therefore unavailable). Since the surface area available for hairpin attaching onto the Ag substrates was less than 50% of the surface area available from the planar Au substrates and the fluorescence intensity is ~10-fold higher than the fluorescence intensity acquired with the use of planar Au substrates, this indicates that the signal enhancement that was observed on the nanostructured Ag film was induced by the Ag NPs rather than increased fluorophore density.

Figure 10:
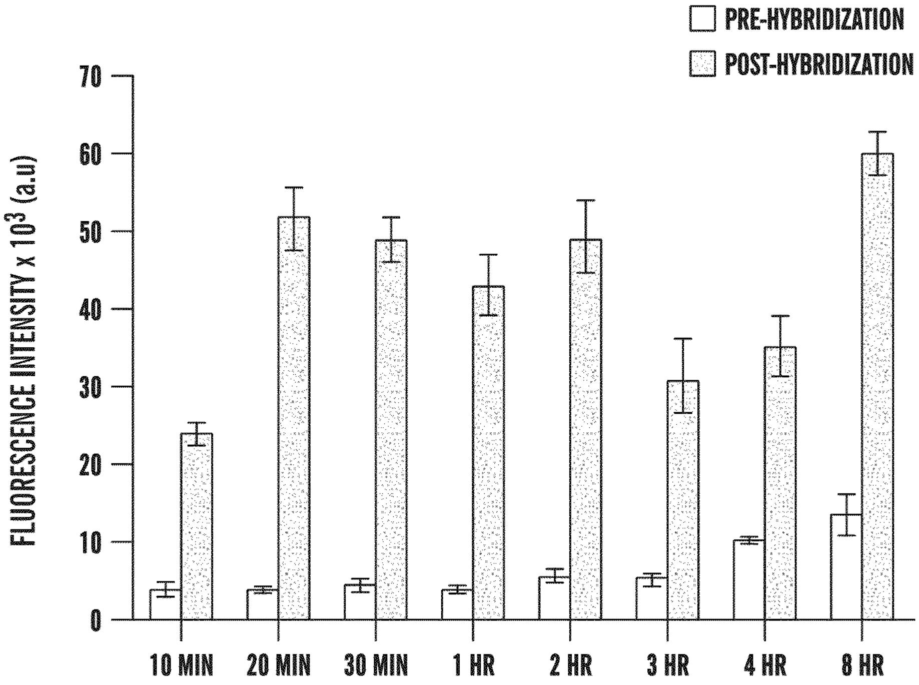
FIG. 10 shows the fluorescence intensity profile of pre- and post-hybridization states as a function of substrate exposure time to Ag. Substrates were prepared in a 10 mM $AgNO_3$ solution with Ag incubation times of 10 min, 20 min, 30 min, 1 hr, 2 hr, 3 hr, 4 hr, and 8 hr. Error bars represent standard deviation. N=4 (2 substrates×2 spots/substrate). CCD integration time: 1 second.
Figure 11:
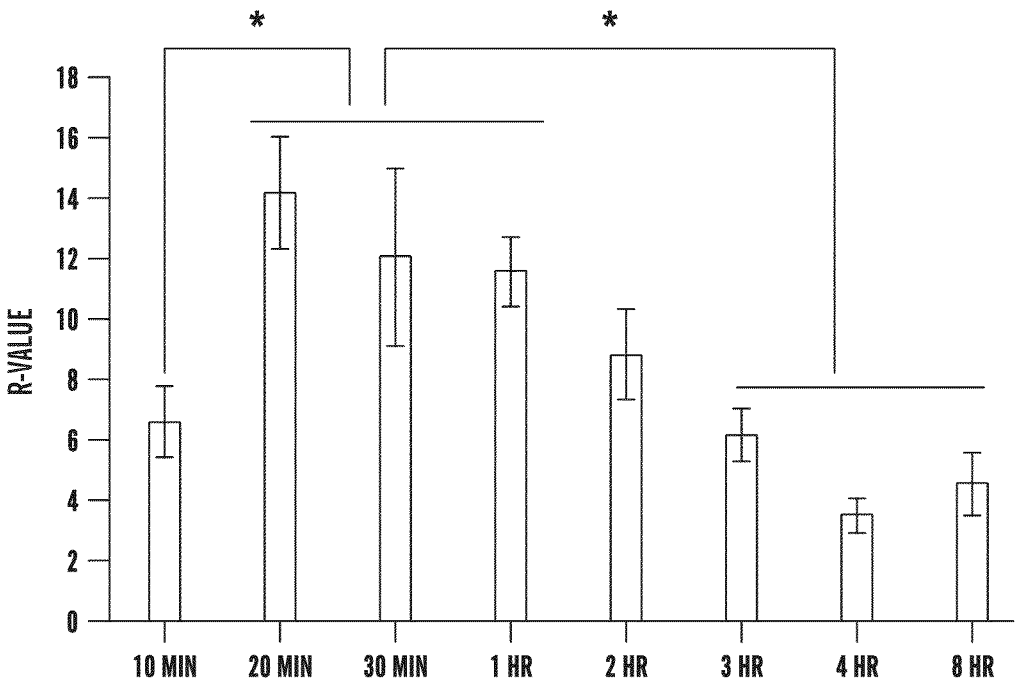
FIG. 11 shows the calculated R-value as a function of substrate exposure time to Ag (10 min, 20 min, 30 min, 1 hr, 2 hr, 3 hr, 4 hr, and 8 hr). Error bars represent standard deviation, N=4 (2 substrates×2 spots/substrate). Statistical analysis was performed using one-way ANOVA with turkey post hoc test, $P<0.05$, Matlab.

The effect of NP surface coverage on the detection performance was examined by testing DNA hybridization response on substrates prepared with different Ag exposure times. FIG. 10 shows the pre-(grey) and post-(black) fluorescence intensity as a function of Ag exposure time. The calculated R-values from all substrate groups were also calculated and are shown in FIG. 11. As one can see from FIG. 11, the R-value increased dramatically from ~6.7-fold to 14-fold (statistically significant) as the Ag exposure time employed in chip preparation increased from 10 to 20 min. The lower R value obtained from the 10 min exposure group was due mainly to the low post-hybridization intensity (shown in FIG. 10; notice the similar pre-hybridization signal between 10 min and 20 min group, as opposed to a dramatic increase in the post-hybridization signal from 10 min to 20 min), which indicates that the 10 min Ag film did not provide an adequate Ag surface area for attachment of the hairpin DNA probes. Notably, R-value dropped dramatically from ~14-fold to 4.5-fold (statistically significant) as the exposure time increased from 20 min to 8 hr. Substrates prepared with an 18 hr Ag exposure resulted in a R-value as low as 1.

The unexpected decrease in R-value obtained from substrate prepared with longer (≥3 hr) Ag exposure time results primarily from decreased quenching (e.g., higher signal pre-target application as shown in FIG. 10). Although this result seemed counter-intuitive (one might expect that the performance of the substrate would increase as the surface area available increases), steric crowding that can occur as the NP coverage increases (a result of an increasing Ag exposure time) can potentially allow probes to wrap around each other, or form duplexes with each other if the local density is high enough. (Maxwell et al., *J. Am. Chem. Soc.* 124:9606-9612 (2002); Zhang et al., *J. Am. Chem. Soc.* 128:8575-8580 (2006), each of which is hereby incorporated by reference in its entirety). All of these scenarios can restrict the probes from forming hairpin structures and result in poor performance. A relatively low Ag exposure time directly lowered both the amount and the size of the Ag NPs that were deposited onto the substrate surface, which indirectly created more space between hairpin probes immobilized on the surface, thus alleviating the steric effect.

Example 3

Role of Surface Blocking Agent with Ag Nanoparticle Film

Earlier studies with planar Au substrate demonstrated the importance of adding a surface blocking agent, mercaptopropanol, as a competitive spacer molecule between probe DNA to mitigate the steric effect (Du et al., *J. Am. Chem. Soc.* 127:7932-40 (2005), which is hereby incorporated by reference in its entirety). To find out if the finding still holds in the new nanoparticles films, the effect of MP concentration on detection performance was examined. In this experiment, the ratio of [MP]/[DNA] was varied from 0 to 25 ([DNA] represents probe DNA concentration, which was held constant at 300 nM). Lowering the ratio of [MP] to [DNA] from 1 with the use of Au planar substrates resulted in poor performance; specifically, high background signals were measured (Du et al., *J. Am. Chem. Soc.* 127:7932-40 (2005), which is hereby incorporated by reference in its entirety). Surprisingly, the opposite results were observed with the use of the nanostructured Ag film. Better performance was observed when the [MP] to [DNA] was lowered from 1. It is believed that the Ag NPs deposited onto the glass surface effectively serve as spacers between the probes, helping to alleviate the steric effect. Therefore, it is believed that the probe density/surface coverage can be controlled via governing the NP density on the substrate surface.

Example 4

The Effect of Oligonucleotide Length

Fluorescence enhancement by metallic NPs is a result of the near-field interaction between the excited-state fluorophore and an enhanced electric-field surrounding the metal particles, which is induced by the incident light. Lakowicz et al. have used finite-difference time-domain (FDTD) calculations to show that the magnitude of the electric field surrounding the particles decays significantly away from the surface of the Ag nanoparticle (Zhang et al., *Nano Lett.* 7:2101-2107 (2007), which is hereby incorporated by reference in its entirety). Schatz et al have also illustrated the dependence of the electric field intensity surrounding an Ag NP on the distance relative to the Ag surface as calculated based on Mie theory (Kelly et al., *J. Phy. Chem. B.* 107:668-677 (2003), which is hereby incorporated by reference in its entirety).

If the magnitude of the electric field in proximity to the Ag nanoparticles is indeed distance dependent, the fluorescence intensity of the fluorophore should also vary at different locations relative to the Ag surface, and one should be able to determine an optimal distance for fluorescence enhancement. In this system, the fixed distance between the fluorophore and the Ag surface (at post-hybridization state in a DNA duplex form) can be adjusted and determined by varying the number of nucleotides in the DNA, given that the persistence length of the duplex DNA is ~50 nm in solution. (Garcia et al., *Biopolymers* 85(2):115-130 (2007); Gueroui et al., *Phys.l Rev. Lett.* 93(16): 166108-11 (2004), each of which is hereby incorporated by reference in its entirety). Therefore, hairpin probes with different numbers of nucleotides ranging from 18mer to 47mer were designed as listed in Table 2. The minimum and maximum duplex lengths listed in Table 2 were calculated assuming free rotation of the fluorophore, where the fluorophore can potentially fold toward (|Duplex Length|−|C6|, min) or away (|Duplex Length|+|C6|, max) from the backbone of the DNA (distance rise per base pair: 0.34 nm; C—C bound length: 0.15 nm) (Voet, *Biochemistry,* 2nd ed., J. Wiley & Sons, New York (1995), pp. 1109, 1361; Chemical Rubber Company., *Handbook of Chemistry and Physics*, CRC Press, Boca Raton, Fla. (2004), p. 116, each of which is hereby incorporated by reference in its entirety).

Probe sequences were obtained from National Center for Biotechnology Information (NCBI) database and were analyzed by RNAstructure v4.5 to generate secondary structures for RNA and DNA using Turner-Zucker algorithm (Mathews et al., *Proc. Natl. Acad. Sci. U.S.A* 101:7287-7292 (2004); Strohsahl et al., *Biosens Bioelectron* 23:233-40 (2007); U.S. Pat. No. 7,442,510 to Miller et al., each of which is hereby incorporated by reference in its entirety). All DNA probes used in this example were purchased from Midland Certified Reagent Company (Midland) and all target DNA were purchased from IDT. Probes from Midland also bear a 3'-TMR fluorophore ($Ab_{max}$: 543 nm, $Em_{max}$: 571 nm) and a 5'-thiol (trityl protected form).

TABLE 2

Probe (P) and Target (T) sequences with the pathogen sources and minimum/maximum duplex length

| Name | Sequence | Source | Length (nm) Min | Length (nm) Max |
|---|---|---|---|---|
| 18mer (P) | 5'-(C6thiol)-GTTCCGTCTTGTCG GAAC(TMR)-3' (SEQ ID NO: 3) | *E. coli* K12 gene | 5.4 | 6.9 |

TABLE 2-continued

| Probe (P) and Target (T) sequences with the pathogen sources and minimum/maximum duplex length | | | | |
|---|---|---|---|---|
| 25mer (P) | 5'-(C6thiol)-CGGATCTCGATGA GCTGCAGATCCG(3'-amino C7) (TMR)-3' (SEQ ID NO: 4) | *E. coli* K12 gene | 7.8 | 9.3 |
| 30mer (P) | 5'-(C6thiol)-AGCATAGGGACCG TGCAGAATCCGTATGCT(3'-amino C7)(TMR)-3' (SEQ ID NO: 5) | *E. coli* TIR gene | 9.5 | 11.0 |
| 34mer (P) | 5'-(C6thiol)-TCGTTAGTGTTAGG AAAAAATCAAACACTCGCGA (3'-amino C7)(TMR)-3' (SEQ ID NO: 1) | *B. anthracis* pag gene | 10.8 | 12.3 |
| 38mer (P) | 5'-(C6thiol)-**AAATTT**CTTTCCCA TGATGAGCACCTTTAAAG**AAA** **TTT**(3'-amino C7)(TMR)-3' (SEQ ID NO: 6) | *K. pneumoniae* blaSHV gene | 12.2 | 13.7 |
| 47mer (P) | 5'-(C6thiol)-CGCTCTGGAAATGT TCAATGAGGACTATGTGACAT TCCCCAGGGACG(3'-amino C7)(TMR)-3' (SEQ ID NO: 7) | *E. coli* plasmid pARS3 gene | 15.2 | 16.7 |
| 18mer (T) | 5'-GTTCCGACAAGACGGAAC-3' (SEQ ID NO: 8) | | | |
| 25mer (T) | 5'-CGGATCTGCAGCTCATCGAGATCCG-3' (SEQ ID NO: 9) | | | |
| 30mer (T) | 5'-AGCATACGGATTCTGCACGGTCCCTATGCT-3' (SEQ ID NO: 10) | | | |
| 34mer (T) | 5'-TCGCGAGTGTTTGATTTTTTCCTAACACTAACGA-3' (SEQ ID NO: 2) | | | |
| 38mer (T) | 5'-**AAATTT**CTTTAAAGGTGCTCATCATGGGAAAG**AAATTT**-3' (SEQ ID NO: 11) | | | |
| 47mer (T) | 5'-CGTCCCTGGGGAATGTCACATAGTCCTCATTGAACATTTCC AGAGCG-3' (SEQ ID NO: 12) | | | |

Bold sequences represent the non-target specific sequences that were incorporated at both termini of the oligonucleotides for hairpin formation. The minimum duplex length was calculated assuming the fluorophore was folded towards the backbone of the DNA, and the maximum duplex length was calculated assuming the fluorphore was folded away from the backbone.

Figure 13:
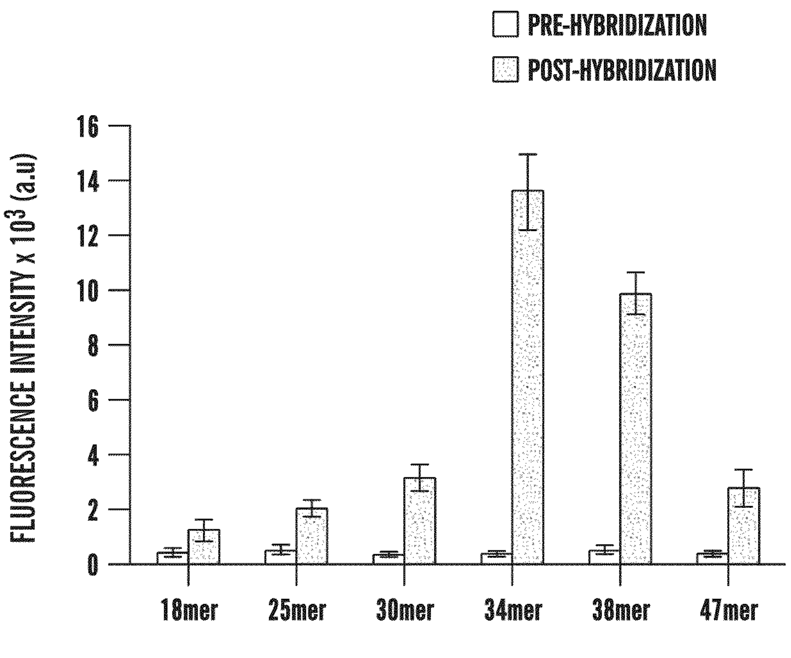
FIG. 13 illustrates the pre- and post-hybridization fluorescence intensity profile of TMR-DNA on the nanostructured Ag film prepared in a 10 mM $AgNO_3$ solution for 1 hr with different probes (18mer, 25mer, 30mer, 34mer, 38mer, and 47mer). [MP] to [Probe DNA]=1:5. N=9 (3 substrates×3 spots/substrate). CCD exposure time: 500 milliseconds.
Figure 14:
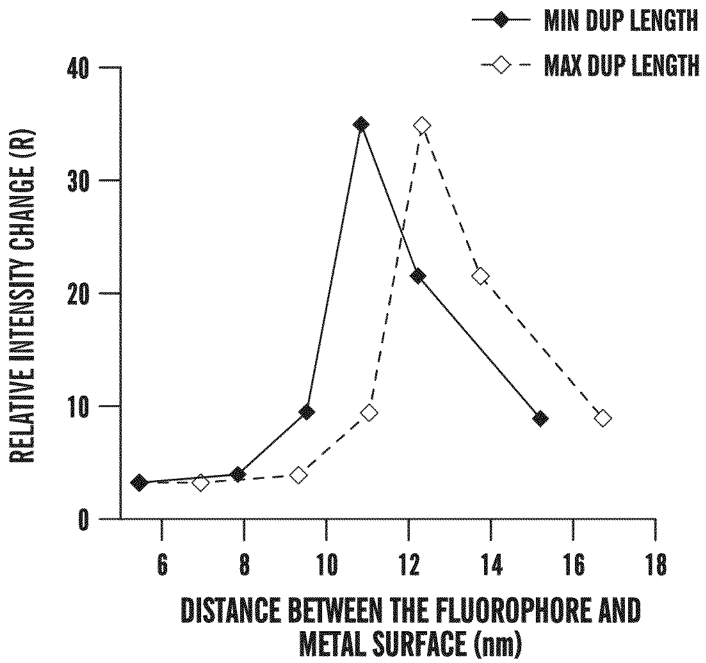
FIG. 14 illustrates the calculated R-value as a function of the distance between the fluorophore and the substrate surface. Substrates were fabricated in a 10 mM $AgNO_3$ solution for 1 hr. [MP] to [Probe DNA]=1:5. N=9 (3 substrates×3 spots/substrate). CCD exposure time: 500 milliseconds. The solid and dashed lines represent the calculated minimum and maximum duplex length, respectively.

Ag substrates used here were all prepared in a 10 mM $AgNO_3$ solution for 1 hr, and subsequently incubated in a probe solution containing 60 nM MP and 300 nM probe DNA in buffered saline, which has been determined to give the highest R-value. Hybridization was allowed to proceed for 18 hr, in order to ensure observed differences were not a result of differences in hybridization efficiency. FIG. 13 shows the fluorescence intensity profile from pre- to post-hybridization with the use of different DNA hairpin probes, and FIG. 14 shows the calculated R-value as a function of the corresponding distance between the fluorophore and the Ag surface. As shown in FIG. 13, the pre-hybridization intensity was consistent among each group, indicating consistent fluorescence quenching and stable hairpin formation. On the contrary, the post-hybridization intensity increased initially from the 18mer to the 30mer, reached a maximum enhancement level of ~35-fold intensity for 34mer, and then decreased at farther distances relative to the Ag surface. This finding agrees with the work conducted by Malicka et al., where a maximum fluorescence enhancement was observed at a distance approximately 90 Å from the Ag surface (Malicka et al., *Analytical Biochemistry* 315(1):57-66 (2003), which is hereby incorporated by reference in its entirety.)

Example 5

Role of Surface Blocking Agent on Nanostructured Ag Film and Planar Au Film

To examine the necessity of including a surface blocking agent in the detection method on different substrates (nanostructured Ag film and planar Au film), the DNA hybridization response on both nanostructured Ag film and planar Au film were measured. The experiment was carried out by measuring the hybridization response as a function of [MP] to [DNA] ratio. Ag nanoparticle film was prepared in 10 mM $AgNO_3$ solution in DMF for 1 hr. Planar Au films having a dimension of 5 mm×5 mm and a thickness of ~25 nm were obtained from Infotonics Inc. (Canandaigua, N.Y.). This experiment employed the previously described probe designated BaPag 1208 (SEQ ID NO: 1) and its target (SEQ ID NO: 2).

Figure 12:
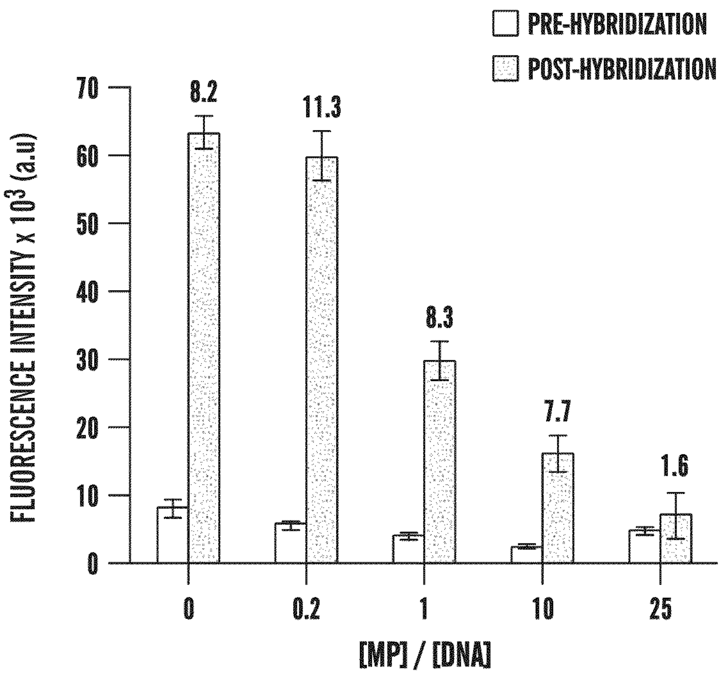
FIG. 12 illustrates fluorescence intensity profile of the DNA detection examined on 1 hr exposure nanostructured Ag film as a function of the ratio of mercaptopropanol concentration [MP] to DNA probe concentration [DNA]. DNA probe concentration was held constant at 300 nM. Number placed on top of each bar represents the corresponding R-value. N=9 (3 spots/substrate×3 substrates). Error bars represent standard deviation. CCD integration time: 1 second.
Figure 15:
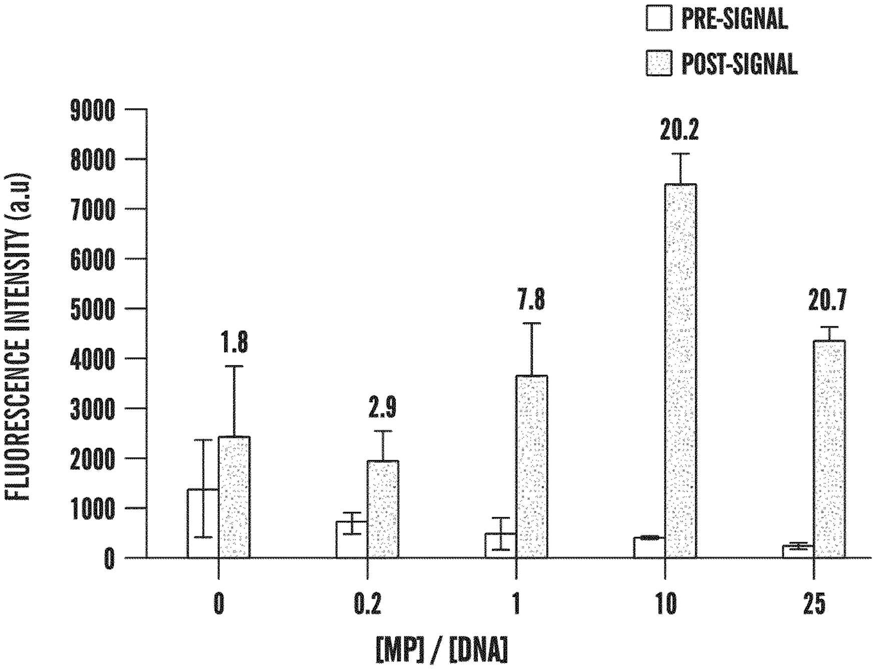
FIG. 15 illustrates the pre- and post-hybridization fluorescence intensity profile upon 1 hr exposure to planar Au substrate as a function of the ratio of mercaptopropanol concentration [MP] to DNA probe concentration [DNA]. DNA probe concentration was held constant at 300 nM. Number placed on top of each bar represents the corresponding R-value. N=9 (3 spots/substrate×3 substrates). Error bars represent standard deviation. CCD integration time: 1 second.

As shown in FIG. 12, an increase in [MP]/[DNA] ratio from 0 to 1 decreased the performance dramatically. The results confirm that NP population at this level helped to alleviate the steric effect that is usually observed from a planar surface. Hence, addition of MP decreased the performance by blocking surface area for the probe to attach to, as indicated by both a decrease in pre- and post-hybridization intensity. In contrast, an increase in [MP]/[DNA] ratio from 0 to 10 increased the performance dramatically for planar Au substrate (FIG. 15). These results are consistent with previous reports (Du et al., *J. Am. Chem. Soc.* 127:7932-40 (2005), which is hereby incorporated by reference in its entirety) demonstrating that the addition of MP in excess helped to alleviate the local steric effect by spacing the probe apart throughout the surface and preventing the probe DNA from attaching on the Au surface.

Example 6

Formation of Nanostructure Ag Substrate on Au Surface

To test whether fluorescence quenching can be enhanced by the presence of a planar Au film when the probe is in the hairpin form, at the same time maintaining the fluorescence signal enhancement derived from the metal nanoparticles at the hybridization state, a metallic composite material was developed in which a planar Au film is coated with Ag nanoparticles.

Planar Au films having a dimension of 5 mm×5 mm and a thickness of ~25 nm were obtained from Infotonics Inc. The planar Au film was first cleaned with piranha solution for 10 minutes. The surface was then prepared by immersing the planar Au film in a 10 mM $AgNO_3$ solution in DMF for 15 and 20 minutes, respectively.

Figure 16:
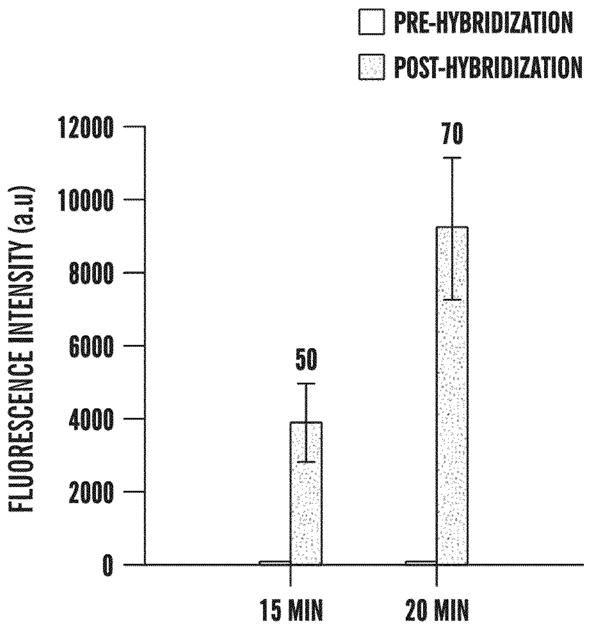
FIG. 16 illustrates the pre- and post-hybridization fluorescence intensity profile upon 15 or 20 min exposure Au film coated with Ag nanoparticles film. DNA probe concentration was held constant at 300 nM; and [MP][DNA]=0.2. DNA target concentration was 2.5 μM. N=9 (3 spots/substrate×3 substrates). Number placed on top of each bar represents the corresponding R-value. Error bars represent standard deviation. CCD integration time: 500 milliseconds.

The DNA hybridization response on planar Au films coated with Ag NPs was measured to determine whether the Au surface provided any additional contribution to the quenching of fluorescence, at the same time maintaining the signal enhancement as a result of LSPR. This experiment employed the previously described probe designated BaPag 1208 (SEQ ID NO: 1) and its target (SEQ ID NO: 2). The probe solution contains 5 parts of DNA probes (300 nM) and 1 part of MP (60 nM). R-values were calculated based on Eq 1. In contrast to the maximal R-values of ~14 with Ag NPs on glass, and ~20 with planar Au substrate, R-values that were three- to six-fold higher were obtained using Ag NPs coated onto an Au surface (FIG. 16). The increase in performance is believed to be derived from a greater quenching due to the underlying planar Au film.

Example 7

Production of Sensor Using "Silver Mirror" Chemistry

Recently, it was demonstrated that preparation of a silver surface using the Tollens silver mirror reaction leads to a fractal type organization of silver nanoparticles (Pan et al., *J. Phys. Chem. B* 110:17383-17387 (2006); Wang et al., *Proc. Natl. Acad. Sci. USA,* 100:8638-8643 (2003), each of which is hereby incorporated by reference in its entirety). Further, these fractal type surfaces (and only such surfaces) consistently support single molecule Raman scattering, due to the intense localization of electric field strength at the few nanometer scale caused by the disordered fractal geometry. This recently discovered effect has been exploited for enhancement of the molecular beacon fluorescence signal.

Glass slides will be cleaned with piranha solution and rinsed with distilled water. Prior to performing silver mirror chemistry, a chromium layer will be formed on the glass slide to promote adhesion between the silver mirror and the glass slide. Chromium deposition will be performed using a Denton Vacuum Evaporator, at a rate of 0.2 nm/s to form a 7 nm Cr layer deposit (Du et al., *J. Am. Chem. Soc.* 127:7932-40 (2005), which is hereby incorporated by reference in its entirety). The coated glass slide will be cleaned with piranha solution and rinsed with distilled water.

75 ml of 0.8 M KOH will be mixed with 75 ml of 0.2 M $AgNO_3$ to form a brown precipitate. 15 M concentrated ammonium hydroxide will be added dropwise to redissolve the precipitate via formation of $[Ag(NH_3)_2]^+$. Dextrose will be added to the solution to a concentration of 0.25 M, and the chromium-coated glass slides will be left in this solution for either 4 min, 10 min., 30 min., or 1 hour. Device performance is expected to be dependent on the amount of Ag present on the surface. Attachment of thiolated hairpins to the silver surface will be carried out as described above (with and without MP, and at various concentrations), and measurement of target binding will be carried out using the approach described in Examples 2-5.

Example 8

Production of Sensor Using Nanosphere Lithography

Glass substrates will be cleaned with piranha etch solution (4:1 concentrated $H_2SO_4$/30% $H_2O_2$) overnight at room temperature, and then rinsed thrice with 18 MΩ water from a Barnstead "nanopure" filtration system. 5 μl of carboxyl terminated polystyrene nanospheres (Interfacial Dynamics Corporation) with diameter D=400 nm will be drop cast onto the glass substrate. Slow evaporation of the water will cause the nanospheres to self assemble into a hexagonally close packed monolayer. The nanosphere monolayer acts as a mask for deposition of evaporated silver or gold. Using a Denton Vacuum Evaporator (DV-502A) equipped with a quartz crystal microbalance, films of silver or gold will be deposited onto the substrate at a rate of 0.2 nm/s to a thickness of 50 nm. Subsequent sonication in ethanol will remove the spheres, leaving behind an array of triangularly shaped metal nanoparticles of various heights (Haynes et al., *J. Phys. Chem. B,* 105, 5599-5611 (2001), which is hereby incorporated by reference in its entirety). These initial conditions will be chosen to produce triangles with a thickness t~50 nm and an in plane triangle height $h=1.5(\sqrt{3}-1-1/\sqrt{3})D=93$ nm for D=400 nm (Haynes et al., *J. Phys. Chem. B,* 105, 5599-5611 (2001), which is hereby incorporated by reference in its entirety). Such particles should have a broad surface plasmon resonance peaked at ~560 nm, ideal for exciting visible organic fluorophores such as rhodamine (Haynes et al., *J. Phys. Chem. B,* 105:5599-5611 (2001), which is hereby incorporated by reference in its entirety).

It is known that exposure of silver nanoparticles to solvent and/or surface adsorbates causes shifts in the surface plasmon resonance frequency through changing their shape and local dielectric environment, respectively (Haynes et al., *J. Phys. Chem. B,* 105, 5599-5611 (2001); Haes et al., *J. Am. Chem. Soc.,* 124, 10596-10604 (2002); Haes et al., *J. Phys. Chem. B,* 108, 109-116 (2004), each of which is hereby incorporated by reference in its entirety). Although the surface plasmon has a large spectral width, it is possible that exposure to the phosphate buffer and/or binding by the thiolated DNA probes will shift the surface plasmon resonance frequency out of resonance with the rhodamine dye. However, such spectral changes in the plasmon resonance are reproducible and have been accurately modeled with theory (Haes et al., *J. Phys. Chem. B,* 108, 109-116 (2004), which is hereby incorporated by reference in its entirety). Thus, they can be easy corrected. For example, using smaller (larger) sized polystyrene nanospheres (a wide range of sizes from 20 nm to several microns are available commercially from Interfacial Dynamics Corporation) will lead to smaller (or larger) values of h and thus will shift the plasmon resonance to the blue (or red) in accordance with optical Mie theory. Similarly, decreasing or increasing the thickness will shift the plasmon resonance to the blue or red, respectively.

Silver nanoparticles are ideal because: 1) silver has the largest electric field enhancement relative to other possible metals such as gold or platinum, and 2) the chemistry to attach the thiolated DNA hairpins to silver is the same as that for gold. However, one can also use an analogous procedure to produce a surface array of gold nanoparticles. Although gold has a surface plasmon resonance frequency different from silver for a given particle size, it is well established that this plasmon resonance is also a strong function of gold particle size and shape (Storhoff et al., *J. Am. Chem. Soc.,* 122, 4640-4650 (2000), which is hereby incorporated by reference in its entirety). Thus, it should be possible to tune the plasmon resonance frequency for gold nanoparticles films, or an other metal nanoparticle film for that matter, in a similar manner described above.

Attachment of thiolated hairpins to the silver surface will be carried out as described above (with and without MP, and at various concentrations), and measurement of target binding will be carried out using the approach described in Examples 2-5.

In addition to the foregoing examples, it should be appreciated that additional design considerations can be implemented. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A sensor chip comprising:

a substrate at least a portion of which is covered by a metal nanoparticle film, wherein the metal nanoparticle film comprises nanoparticles covalently attached to the substrate, the nanoparticles having a size in the range of 3.6 to 31.4 nm in diameter, and the metal nanoparticle film having a surface roughness of between about 0.7 nm and about 3 nm;

a first nucleic acid molecule that is characterized by being able to (i) self-anneal into a hairpin conformation and (ii) hybridize specifically to a target nucleic acid molecule, the first nucleic acid molecule having first and second ends, which first end is tethered to the metal nanoparticle film; and a fluorophore bound to the second end of the first nucleic acid molecule;

whereby when the first nucleic acid molecule is in the hairpin conformation, the metal nanoparticle film substantially quenches fluorescent emissions by the fluorophore, and when the first nucleic acid molecule is in a non-hairpin conformation fluorescent emissions by the fluorophore are surface plasmon-enhanced and yield an R-value of at least about 3.4.

2. The sensor chip according to claim 1 wherein the metal nanoparticle film comprises a surface roughness of between about 1 nm and about 2.4 nm.

3. The sensor chip according to claim 1 wherein the metal nanoparticle film comprises a surface roughness of between about 1 nm and about 2 nm.

4. The sensor chip according to claim 1 wherein the metal nanoparticle film is translucent.

5. The sensor chip according to claim 4 wherein the metal nanoparticle film is less than about 50 nm thick.

6. The sensor chip according to claim 1 wherein the metal nanoparticle film comprises gold, silver, platinum, titanium, copper, gallium, or aluminum.

7. The sensor chip according to claim 1 wherein the first nucleic acid molecule is less than about 60 nucleotides in length.

8. The sensor chip according to claim 1 wherein the fluorophore is a dye, a protein, or a semiconductor nanocrystal.

9. The sensor chip according to claim 1 wherein the substrate is light transmissive.

10. The sensor chip according to claim 1 wherein the substrate is capable of quenching fluorescence of the fluorophore.

11. The sensor chip according to claim 1 wherein the substrate is a metal and is different from the metal used for the metal nanoparticle film.

12. The sensor chip according to claim 11 wherein the metal nanoparticle film comprises silver nanoparticles and the substrate comprises gold, platinum, titanium, copper, gallium, or aluminum.

13. The sensor chip according to claim 1 wherein the sensor chip comprises:

a plurality of nucleic acid molecules that are different from one another and are characterized by being able to (i) self-anneal into a hairpin conformation and (ii) hybridize specifically to a target nucleic acid molecule, each of the plurality of nucleic acid molecules having first and second ends, which first end is tethered to the metal nanoparticle film; and a fluorophore bound to the second end of each of the plurality of nucleic acid molecules;

whereby when the nucleic acid molecules are in the hairpin conformation, the metal nanoparticle film substantially quenches fluorescent emissions by the fluorophore bound thereto, and when the nucleic acid molecules are in a non-hairpin conformation fluorescent emissions by the fluorophore bound thereto are surface plasmon-enhanced and yield an R-value of at least about 3.4.

14. The sensor chip according to claim 13, wherein the plurality of nucleic acid molecules are present in the form of an array.

15. A biological sensor device comprising:

a sensor chip according to claim 1;

a light source that illuminates the sensor chip at a wavelength suitable to induce fluorescent emissions by the fluorophore(s); and a detector positioned to detect fluorescent emissions by the fluorophore(s).

16. The biological sensor device according to claim 15, wherein the sensor chip is positioned in a flow cell with the chip surface comprising the portion covered by the metal nanoparticle film exposed to the interior of the flow cell.

17. The biological sensor device according to claim 16 wherein the metal nanoparticle film is light transmissive, and the light source is positioned to illuminate the sensor chip from a side thereof that is opposite the chip surface comprising the portion covered by the metal nanoparticle film.

18. The biological sensor device according to claim 16 wherein the metal nanoparticle film is light transmissive, and the detector is positioned to detect fluorescent emissions emanating from the chip surface comprising the portion covered by the metal nanoparticle film.

19. A method of detecting the presence of a target nucleic acid molecule in a sample comprising:

exposing the sensor chip according to claim 1 to a sample under conditions effective to allow any target nucleic acid molecule in the sample to hybridize to the nucleic acid molecules, causing the nucleic acid molecules to adopt the non-hairpin conformation;

illuminating the sensor chip with light sufficient to cause emission of fluorescence by the fluorophore(s); and determining whether or not the sensor chip emits fluorescent emissions of one or more of the fluorophores upon said illuminating, wherein fluorescent emission by the sensor chip indicates that a nucleic acid molecule is in the non-hairpin conformation and therefore that its target nucleic acid molecule is present in the sample.

20. The method according to claim 19 wherein the target nucleic acid molecule is specific for a pathogen, a disease state, a genetic marker, or a forensic target, or associated with a breeding trait for a plant or animal.

21. The sensor chip according to claim 1 wherein the metal nanoparticle film comprises a nanoparticle density of between 315 to 722 nanoparticles per $\mu m^2$ as measured by atomic force microscopy.

22. The sensor chip according to claim 1 wherein the metal nanoparticle film has an average particle size of about 4.9 nm to about 6.93 nm.

23. The sensor chip according to claim 1 wherein the sensor comprises an R-value of at least about 6.

24. The sensor chip according to claim 1 wherein the nanoparticles are covalently attached to the substrate via a linker molecule.

* * * * *